United States Patent

Harada et al.

[11] Patent Number: 6,143,917
[45] Date of Patent: Nov. 7, 2000

[54] PROCESS FOR PRODUCING ARYL CARBAMATES

[75] Inventors: Katsumasa Harada; Ryoji Sugise; Kohichi Kashiwagi; Tsunao Matsuura, all of Ube, Japan

[73] Assignee: Ube Industries, Ltd., Ube, Japan

[21] Appl. No.: 09/171,076

[22] PCT Filed: Feb. 13, 1998

[86] PCT No.: PCT/JP98/00592

§ 371 Date: Oct. 13, 1998

§ 102(e) Date: Oct. 13, 1998

[87] PCT Pub. No.: WO98/35936

PCT Pub. Date: Aug. 20, 1998

[51] Int. Cl.⁷ .................................................. C07C 269/04
[52] U.S. Cl. .................... 560/32; 560/11; 560/13; 560/17; 560/27; 560/29; 560/115; 560/132; 560/137
[58] Field of Search .................. 560/11, 13, 17, 560/27, 29, 32, 115, 132, 137

[56] References Cited

U.S. PATENT DOCUMENTS 4,097,676  6/1978  Romano .................................. 560/132

FOREIGN PATENT DOCUMENTS 47-11562  6/1972  Japan .
52-136147 11/1977  Japan .
1-230550  9/1989  Japan .

OTHER PUBLICATIONS

J. Polym. Sci., Polym. Chem. Ed. vol. 17 (3), pp. 835–841 (1979).
"Reaction of Diphenyl Carbonate With Amines . . . ,", Inst. Pry. Urethan, 2 pp. 61–65 (1980).
Synthesis, pp. 423–425 (Jun. 1989).
Chem. Ber., 99, pp. 1576–1579 (1966).
Synth. Commun., 26(2), pp. 331–349 (1996).
Tetrahedron, vol. 51, No. 29, pp. 8073–8088 (1995).

*Primary Examiner*—Johann Richter
*Assistant Examiner*—Brian J. Davis
*Attorney, Agent, or Firm*—Finnegan, Henderson, Farabow, Garrett & Dunner, L.L.P.

[57] ABSTRACT

A process for producing an aryl carbamate of a high purity at a high yield by reacting a diaryl carbonate with an amine compound having one or more hydrogen atoms bonded to the N position in the presence of carboxylic acid(s) of the following general formulae (I): $R^1$—COOH and/or (II): $R^2$—COOH (wherein $R^1$ represents an alkyl or cycloalkyl group having an α-positioned carbon atom bonded to only one hydrogen atom, an alkyl group having an α-positioned carbon atom bonded to no hydrogen atom, or an aryl or heterocyclic group, and $R^2$ represents an alkyl group having an α-positioned carbon atom bonded to two or more hydrogen atoms).

17 Claims, No Drawings

PROCESS FOR PRODUCING ARYL CARBAMATES

This application is a 321 of PCT/JP98/00592 filed Feb. 13, 1998.

TECHNICAL FIELD

The present invention relates to a process for producing an aryl carbamate from a diaryl carbonate with a high selectivity and with a high yield.

The aryl carbamates are compounds useful in a wide range uses, as for example, pharmaceuticals, agricultural chemicals and materials for the synthesis thereof, as various fine chemicals and materials for the synthesis thereof and as reagents for analysis.

BACKGROUND ART

As processes for producing carbamates, (1) a process of reacting an isocyanate with an alcohol, (2) a process of reacting a chloroformate ester with an amine in the presence of a base, (3) a process of reacting phosgene with an alcohol and an amine, and (4) a process of reacting urea with an alcohol, are generally known.

However, these conventional processes are disadvantageous in that in the process (1), the isocyanate is stimulative and is difficult to handle; in the process (2), the base must be used in an molar amount equal to or more than that of the reactive compounds; in the process (3), phosgene exhibits a high toxicity and a base must be used for the reaction; and in the process (4), the reaction must be carried out at a high temperature under a high pressure.

On the other hand, as processes for producing aryl carbamates from diaryl carbonates, (5) a process of reacting a diaryl carbonate with an aromatic amine compound in the presence of a heterocyclic monocyclic tertiary amine compound, such as 2-hydroxypyridine, as disclosed in Japanese Unexamined Patent Publication No. 52-136,147, J. Polym. Sci., Polym. Chem. Ed., 17(3), 835 (1979), and Inst. Prog. Urethan, 2, 61 (1980), (6) a process of reacting a diaryl carbonate with an aliphatic amine compound without the presence of a catalyst, as disclosed in U.S. Pat. No. 4,097, 676), (7) a process of reacting bis(4-nitrophenyl)carbonate with an aliphatic amine compound and aniline in methylene chloride, as disclosed in Synthesis, 423 (1989), (8) a process of reacting bis(2,4-dinitrophenyl)carbonate with amino acid ester, as disclosed in Chem. Ber., 99, 1576 (1966), (9) a process of reacting an asymmetric bis(nitro-substituted aryl) carbonate with an aliphatic primary amine compound as disclosed in Synth. Commun., 26 (2), 331 (1996), (10) a process of reacting diphenyl carbonate with an aromatic amine compound in the presence of an organic phosphoric acid, trifluoro-methanesulfonic acid, trifluoroacetic acid, propionic acid or an aromatic amine-hydrochloric acid salt, as disclosed in Tetrahedron, 51, 8073 (1995), (11) a process of reacting a diaryl carbonate with a primary or secondary polyamine in the presence of a Lewis acid catalyst, as disclosed in Japanese Unexamined Patent Publication No. 47-11,562, and (12) a process of reacting a diaryl carbonate with an alkylpolyamine, as disclosed in Japanese Unexamined Patent Publication No. 1-230,550, are known.

These processes are, however, disadvantageous in the following problems. In the process (5), the catalyst, which is expensive, must be used in an molar amount equal to or more than the molar amount of the reactive materials, the reaction rate is slow and, when the reaction temperature is raised to increase the reaction rate, urea derivatives are produced, as by-products, in a large amount. In the process (6), when an aromatic amine compound or other amine compound having a high stereostructual volume is used, the reactivity of the amine compound with the diaryl carbonate is very low, and when the reaction temperature is raised to enhance the reactivity of the amine compound, urea derivatives are produced, as by-products, in a large amount. In the process (7), although when the aliphatic primary amine compound is used a relatively good result can be obtained, when the secondary amine compound, which has a high steric hindrance, is used, the reaction rate is slow and, especially, when an aromatic amine (aniline) is used, the reaction rate is very slow and the yield is unsatisfactory. In the process (8), the amino acid ester to be used as a starting material is limited to a primary amino acid ester which can easily react even without the presence of a catalyst. In the process (9), the starting amine compound is limited to an aliphatic primary amine compound. In the process (10), there is a problem in the catalyst usable for the process. Namely, although an organic phosphoric acid is a most effective catalyst, this compound is disadvantageous in that the price is very high. Also, catalysts other than an organic phosphoric acid result in a slow reaction rate. Further, when trifluoroacetic acid or propionic acid is used as a catalyst, these catalyst compounds react with the amine to produce an acid amide, as a by-product, and thus the yield of the target product disadvantageously decreases. Further, in the processes (5), (11) and (12), there are disadvantages in that since a polyamine having two or more amino groups is used, the reaction is carried out in two or more steps, and thus the reaction time is longer than that in the production of the carbamate from the monoamine compound, and by-products (urea derivatives) are easily produced during the reaction steps. Also, in the processes (5), (11) and (12), there are problems that when the reaction temperature is raised to increase the reaction rate, the urea derivatives, and allophanates, biurets and trimers derived from decomposition of the carbamates, are produced and thus the yield of the target compound decreases, and that when the aromatic polyamine compounds or other polyamine compounds having a high stereostructual volume are employed, they exhibit a very low reactivity. Therefore, when the yield of the target compound is low and the by-products are produced, there is an inevitable problem that it is very difficult to isolate the resultant target compound from the reaction product mixture. Further, in the process (11), there is a problem that the reaction vessel is corroded by the Lewis catalyst.

As mentioned above, the conventional carbamate production processes have various problems.

Namely, the processes (1) to (4) have problems derived from the starting materials, namely the starting materials having a high stimulation or toxicity, or the base must be used, or problems derived from reaction conditions, namely the reaction must be carried out at a high temperature or under a high pressure.

The processes (5) and (6) have a problem in that the reactivity is variable in response to the type of the amine compound applied to the reaction, especially when an aromatic amine compounds or other amine compounds having a high stereostructual volume are used, the reactivity decreases and urea derivatives are produced as by-products. Therefore, particularly when the aromatic amine compounds and other amine compounds having a high stereostructual volume are employed, it is difficult to produce the carbamate at a high reaction rate, with a high selectivity and with a high yield. Further, the process (10) has big problems in that the catalyst is expensive, that the reaction rate is slow that and acid amides are produced as by-products.

DISCLOSURE OF THE INVENTION

An object of the present invention is to provide a process for producing a carbamate, free from the above-mentioned problems. Namely, the object of the present invention is to provide a process for producing an aryl carbamate from a diaryl carbonate and an amine compound having at least one hydrogen atom located at an N-position under moderate conditions at a high reaction rate with a high selectivity and with a high yield.

Another object of the present invention is to provide a process for producing an aryl carbamate in a condition in which the resultant aryl carbamate can be easily isolated and collected, from a diaryl carbonate and an amine compound having at least one hydrogen atom located at a N-position.

The process of the present invention for producing an aryl carbamate is characterized by reacting a diaryl carbonate with an amine compound having at least one hydrogen atom located at an N-position in the presence of at least one member selected from the carboxylic acids of the formulae (I) and (II):

$$R^1\text{—COOH} \qquad (I)$$

and $$R^2\text{—COOH} \qquad (II)$$

In the formulae (I) and (II), $R^1$ represents (1) an alkyl or cycloalkyl group having an α-positioned carbon atom bonded to the —COOH group and to only one hydrogen atom, (2) an alkyl group having an α-positioned carbon atom bonded to the —COOH group and to no hydrogen atom, or (3) an aryl group or a heterocyclic group;

$R^2$ represents an alkyl group having an α-positioned carbon atom bonded to the —COOH group and to at least two hydrogen atoms.

In the process of the present invention, the amine compound usable for the reaction is selected from the group consisting of the compounds represented by the formulae (III), (IV), (V), (VI), and (VII);

$$R^3\text{—NH}_2 \qquad (III)$$

$$R^4\text{—NH—R}^5 \qquad (IV)$$

$$R^6\text{—NH—Ar}^1\text{—(X)}_x\text{—(R}^7)_y\text{—(Z)}_z\text{—Ar}^2\text{—NH—R}^8 \qquad (V)$$

$$R^9\text{—NH—R}^{10}\text{—NH—R}^{11} \qquad (VI)$$

(VII)

in which formulae (III) to (VII), $R^3$ represents a member selected from aralkyl groups, aryl groups and heterocyclic groups;

$R^4$ and $R^5$ respectively and independently from each other represent a member selected from alkyl groups, aralkyl groups, aryl groups and heterocyclic groups, wherein each of these groups may have one or more substituents and $R^4$ and $R^5$ may be fuse-bonded with each other to form a fused cyclic structure;

$R^6$ and $R^8$ respectively and independently from each other represent a member selected from alkyl groups and aralkyl groups, each of which groups may have one or more substituents;

$Ar^1$ and $Ar2$ respectively and independently from each other represent a member selected from arylene groups each of which may have one or more substituents;

$R^7$ represents a member selected from alkylene groups, alkenylene groups, aralkylene groups and arylene groups, each of which groups may have one or more substituents;

X and Z respectively and independently from each other represent a divalent group selected from alkylene groups, and —NH—, —O—, —S—, —SS—, —$SO_2$— and —CO— groups, wherein the alkylene groups each may have one or more substituents;

x, y and z respectively and independently from each other represent an integer of 0 or 1;

$R^9$ and $R^{11}$ respectively and independently from each other represent a member selected from a hydrogen atom, alkyl groups, aralkyl groups and aryl group, wherein each of the alkyl, aralkyl and aryl groups may have one or more substituents;

$R^{10}$ represents a member selected from alkylene groups, aralkylene groups, and arylene groups, each of which groups may have one or more substituents; and the compounds of the formula (VII) may have one or more substituents.

In the reaction of the process of the present invention, the carboxylic acid of the formula (I) is fed in a molar amount of 0.005 to 5 times the molar amount in which the diaryl carbonate is fed, and at least one member selected from the amine compounds of the formulae (III) and (IV) is fed in a molar amount of 0.05 to 20 times the molar amount in which the diaryl carbonate is fed.

In the reaction of the process of the present invention, at least one amine compound selected from those represented by the formulae (V) to (VII) is used, and the carboxylic acid is used in a feeding molar amount of 0.01 to 5 times the feeding molar amount of the above-mentioned amine compound.

In the reaction of the process of the present invention, the carboxylic acid of the formula (II) is used in a feeding concentration of 0.005 mole/liter or more, at least one amine compound selected from those of the formulae (III) and (IV) is used in a feeding concentration of 0.5 mole/liter or more, and the diaryl carbonate is used in a feeding concentration of 0.5 mole/liter or more.

In the process of the present invention, after the reaction is completed, the resultant reaction product-containing mixture may be cooled to a temperature of 40° C. or less, to cause the target aryl carbamate to precipitate from the mixture, and the precipitated aryl carbonate may be isolated and collected from the mixture.

Also, in the process of the present invention, after the reaction is completed, a non-reacted portion of the amine compound may be removed from the reaction product-containing mixture, and then the target aryl carbonate may be isolated and collected from the non-reacted amine compound-removed mixture.

BEST MODE OF CARRYING OUT THE INVENTION

In the process of the present invention, an aryl carbamate is produced by reacting a diaryl carbonate with an amine compound having at least one hydrogen atom bonded to an N-position of the amine compound in the presence of at least one carboxylic acid selected from those of the above-mentioned formulae (I) and (II).

The two aryl groups of the diaryl carbonate usable for the process of the present invention may be the same as each other or may be different from each other, or may be substituted by one or more substituents or no substituent. In the case where the aryl groups have two or more substituents, these substituents may be the same as each other or different from each other.

The substituents, which may be contained in the aryl groups of the aryl carbonate usable for the process of the present invention, are preferably selected from alkyl groups having 1 to 12 carbon atoms, for example methyl, ethyl, propyl and butyl groups; aralkyl groups having 7 to 15 carbon atoms, for example, benzyl and phenethyl groups; aryl groups having 6 to 14 carbon atoms, for example, phenyl and tolyl groups; alkoxy groups having 1 to 12 carbon atoms, for example, methoxy, ethoxy, propoxy, butoxy and trifluoromethoxy groups; thioalkoxy groups having 1 to 12 carbon atoms, for example, thiomethoxy and thioethoxy groups; aryloxy groups having 6 to 14 carbon atoms, for example, a phenoxy group; halogen atoms, for example, fluorine, chlorine and bromine atoms; a nitro group, a hydroxyl group, a cyano group, and dialkylamino groups, for example, a dimethylamino group.

The substituted and unsubstituted aryl groups of the diaryl carbonate usable for the present invention include, for example, phenyl, naphthyl, anthranyl, tolyl, xylyl, ethylphenyl, propylphenyl, octylphenyl, nonylphenyl, dodecylphenyl, biphenylyl, methoxyphenyl, dimethoxyphenyl, butoxyphenyl, phenoxyphenyl, chlorophenyl, dichlorophenyl, trichlorophenyl, pentachlorophenyl, bromophenyl, dibromophenyl, tribromophenyl, pentabromophenyl, nitrophenyl, dinitrophenyl, hydroxyphenyl, cyanophenyl and dimethylaminophenyl groups.

Also, these aryl groups include o-, m- and p-isomers, and the substituents attached to the aryl structures include n-, iso-, sec- and tert-isomers.

The diaryl carbonates usable for the present invention include the compounds mentioned below. Namely, the diaryl carbonates having the same unsubstituted aryl groups as each other can be selected from, for example, diphenyl carbonate, di-1-naphthyl carbonate, di-2-naphthyl carbonate and di-9-anthryl carbonate. Also, the diaryl carbonates having the same aryl groups as each other and each substituted with at least one alkyl group having 1 to 12 carbon atoms can be selected from, for example, bis(2-tolyl)carbonate, bis(3-tolyl)carbonate, bis(4-tolyl)carbonate, bis[4-(tert-butyl)phenyl]carbonate, bis(4-octylphenyl)carbonate, bis(4-nonylphenyl)carbonate, and bis(4-dodecylphenyl)carbonate.

The diaryl carbonates having the same aryl groups as each other and respectively substituted with one or more aryl groups having 6 to 14 carbon atoms include, for example, bis(4-biphenylylphenyl)carbonate.

The diaryl carbonates having the same aryl groups as each other and respectively substituted with at least one alkoxy group with 1 to 12 carbon atoms can be selected from, for example, bis(2-methoxyphenyl)carbonate, bis(3-methoxyphenyl)carbonate, bis(4-methoxyphenyl)carbonate, bis(3-butoxyphenyl)carbonate, bis(4-butoxyphenyl)carbonate, and bis(3,5-dimethoxyphenyl)carbonate.

The diaryl carbonates having the same aryl groups as each other and respectively substituted with at least one aryloxy group with 6 to 14 carbon atoms include, for example, bis(4-phenoxyphenyl)carbonate.

The diaryl carbonates having the same aryl groups as each other and respectively substituted with at least one halogen atom include, for example, bis(2-chlorophenyl)carbonate, bis(3-chlorophenyl)carbonate, bis(4-chlorophenyl)carbonate, bis(2,4-dichlorophenyl)carbonate, bis(2,6-dichlorophenyl)carbonate, bis(2,4,5-trichlorophenyl)carbonate, bis(2,4,6-trichlorophenyl)carbonate, bis(pentachlorophenyl)carbonate, and bis(4-bromophenyl)carbonate.

The diaryl carbonates having the same aryl groups as each other and respectively substituted with at least one nitro group include, for example, bis(2-nitrophenyl)carbonate, bis(3-nitrophenyl)carbonate, bis(4-nitrophenyl)carbonate and bis(2,4-dinitrophenyl)carbonate.

The diaryl carbonates having two aryl groups different from each other include, for example, the compounds shown below.

The diaryl carbonates having an unsubstituted aryl group and an aryl group substituted with at least one alkyl group with 1 to 12 carbon atoms can be selected from, for example, 3-tolylphenyl carbonate and 4-tolylphenyl carbonate.

Also, the diaryl carbonates having an unsubstituted aryl group and a substituted aryl group with at least one aralkyl group having 7 to 15 carbon atoms include, for example, 4-benzylphenyl(phenyl)carbonate.

The diaryl carbonates having an unsubstituted aryl group and a substituted aryl group with at least one alkoxy group having 1 to 12 carbon atoms, can be selected from, for example, 4-methoxyphenylphenyl carbonate and 4-ethoxy-1-naphthalenylphenyl carbonate.

The diaryl carbonates having an unsubstituted aryl group and a substituted aryl group with at least one thioalkoxy group having 1 to 12 carbon atoms include, for example, 4-methylthiophenylphenyl carbonate, and the diaryl carbonates having an unsubstituted aryl group and a substituted aryl group with at least one aryloxy group having 6 to 14 carbon atoms include, for example, 4-phenoxyphenylphenyl carbonate.

The diaryl carbonates having an unsubstituted aryl group and a substituted aryl group with at least one halogen atom can be selected from, for example, 2-chlorophenylphenyl carbonate and 4-chlorophenylphenyl carbonate.

The diaryl carbonates having an unsubstituted aryl group and a substituted aryl group with at least one nitro group can be selected from, for example, 3-nitrophenylphenyl carbonate, 4-nitrophenylphenyl carbonate, 2,4-dinitrophenylphenyl carbonate, and 3,4-dinitrophenylphenyl carbonate.

The diaryl carbonates having an unsubstituted aryl group and a substituted aryl group with at least one hydroxyl group, can be selected from, for example, 3-hydroxyphenylphenyl carbonate, and 4-hydroxyphenylphenyl carbonate.

The other diaryl carbonates usable for the process of the present invention include, for example, 4-methoxyphenyl-4'-nitrophenyl carbonate, 4-cyanophenyl-4'-nitrophenyl carbonate, 4-thiomethoxyphenyl-4'-nitrophenyl carbonate, 2-chlorophenyl-4'-nitrophenyl carbonate, 2-dimethylaminophenylphenyl carbonate, 2-bromo-4-cyano-6-nitrophenylphenyl carbonate, and pentabromophenyl-2',4',6'-tribromophenyl carbonate.

Among the diaryl carbonates mentioned above, the diaryl carbonates having the same two aryl groups as each other are advantageously used for the process of the present invention. Among them, diphenyl carbonate, bis(2-tolyl)carbonate, bis(4-chlorophenyl)carbonate, bis(4-nitrophenyl)carbonate, and bis(3,5-dimethoxyphenyl)carbonate are more preferably used and diphenyl carbonate is still more preferably used.

In the process of the present invention, the amine compounds usable for the reaction with the above-mentioned diaryl carbonates have at least one hydrogen atom bonded to the N-position thereof and are preferably selected from the compounds represented by the above-mentioned formulae (III), (IV), (V), (VI) and (VII).

In the formula (III):

$R^3$ represents an aralkyl group preferably aralkyl groups having 7 to 15 carbon atoms, for example, benzyl and phenethyl groups; an aryl group, preferably aryl groups having 6 to 14 carbon atoms, for example, a phenyl group; or a heterocyclic group, for example, a pyridyl group. These aralkyl, aryl and heterocyclic groups may have at least one substituent selected from, for example, alkyl groups, aryl groups, alkoxy groups, thioalkoxy groups, aryloxy groups, halogen atoms, a nitro group and a cyano group.

The monoamine compounds represented by the formula (III) include, for example, the following compounds.

When $R^3$ represents the above-mentioned aralkyl groups:
benzylamine, phenethylamine, and naphthylamine, etc.

When $R^3$ represents the above-mentioned unsubstituted aryl groups:
aniline, 1-naphthylamine, and 2-naphthylamine, etc.

When $R^3$ represents the alkyl group-substituted aryl groups:
2-toluidine, 3-toluidine, 4-toluidine, 2,3-dimethylaniline, 2,4-dimethylaniline, 2,5-dimethylaniline, 2,6-dimethylaniline, 3,4-dimethylaniline, 3,5-dimethylaniline, 2-ethylaniline, 3-ethylaniline, 4-ethylaniline, 2,3-diethylaniline, 2,4-diethylaniline, 2,5-diethylaniline, 2,6-diethylaniline, 3,4-diethylaniline, 3,5-diethylaniline, 4-isopropylaniline, 2-ethyl-6-methylaniline, 2-trifluoromethylaniline, 3-trifluoromethylaniline, 4-trifluoromethylaniline, etc.

When $R^3$ represents the aryl group-substituted aryl groups:
2-aminodiphenyl, 3-aminodiphenyl, 4-aminodiphenyl, etc.

When $R^3$ represents the alkoxy group-substituted aryl groups:
2-anisidine, 3-anisidine, 4-anisidine, 2,3-dimethoxyaniline, 2,4-dimethoxyaniline, 2,5-dimethoxyaniline, 2,6-dimethoxyaniline, 3,4-dimethoxyaniline, 3,5-dimethoxyaniline, 2-methoxy-5-methylaniline, 4-ethoxyaniline, etc.

When $R^3$ represents the thioalkoxy group-substituted aryl groups:
2-methylthioaniline, 3-methylthioaniline, 4-methylthioaniline, etc.

When $R^3$ represents the aryloxy group-substituted aryl groups;
2-aminodiphenylether, 4-aminodiphenylether, etc.

When $R^3$ represents the fluorine atom-substituted aryl groups:
2-fluoroaniline, 3-fluoroaniline, 4-fluoroaniline, 2,3-difluoroaniline, 2,4-difluoroaniline, 2,5-difluoroaniline, 2,6-difluoroaniline, 3,4-difluoroaniline, 3,5-difluoroaniline, etc.

When $R^3$ represents the chlorine atom-substituted aryl groups:
2-chloroaniline, 3-chloroaniline, 4-chloroaniline, 2,3-dichloroaniline, 2,4-dichloroaniline, 2,5-dichloroaniline, 2,6-dichloroaniline, 3,4-dichloroaniline, 3,5-dichloroaniline, 2,4,5-trichloroaniline, 2,4,6-trichloroaniline, etc.

When $R^3$ represents the bromine atom-substituted aryl groups:
2-bromoaniline, 3-bromoaniline, 4-bromoaniline, 2,3-dibromoaniline, 2,4-dibromoaniline, 2,5-dibromoaniline, 2,6-dibromoaniline, 3,4-dibromoaniline, 3,5-dibromoaniline, 2,4,5-tribromoaniline, 2,4,6-tribromoaniline, etc.

When $R^3$ represents the nitro group-substituted aryl groups:
3-nitroaniline, 4-nitroaniline, etc.

When $R^3$ represents the cyano group-substituted aryl groups:
3-cyanoaniline, 4-cyanoaniline, etc.

When $R^3$ represents the alkyl group and halogen atom-substituted aryl groups:
2-chloro-6-methylaniline, 3-chloro-2-methylaniline, 3-chloro-4-methylaniline, 4-chloro-2-methylaniline, 5-chloro-2-methylaniline, 2-chloro-5-trifluoromethylaniline, 4-chloro-2-trifluoromethylaniline, 4-chloro-2,5-dimethylaniline, 4-bromo-2-trifluoromethylaniline, etc.

When $R^3$ represents the alkoxy group and halogen atom-substituted aryl groups:
3-chloro-2-methoxyaniline, 4-chloro-2-methoxyaniline, 5-chloro-2-methoxyaniline, 5-chloro-2,4-dimethoxyaniline, etc.

When $R^3$ represents the aryl groups substituted by at least one member selected from nitro, alkyl and alkoxy groups, halogen atoms and a cyano group:
2-methyl-4-nitroaniline, 4-methyl-3-nitroaniline, 2-methoxy-4-nitroaniline, 2-methoxy-5-nitroaniline, 4-fluoro-2-nitroaniline, 2-chloro-4-nitroaniline, 4-chloro-3-nitroaniline, 2-cyano-4-methyl-6-nitroaniline, etc.

When $R^3$ represents the above-mentioned heterocyclic groups, the monoamine compounds of the formula (III) include the following compounds.

When R represents a pyrrolyl group:
2-amino-3-ethoxycarbonyl-4-phenylpyrrole, etc.

When $R^3$ represents an indolyl group:
2-amino-1-methylindole, 3-amino-5-ethoxy-2-phenylindole, etc.

When $R^3$ represents an pyridyl group:
2-aminopyridine, 3-aminopyridine, 4-aminopyridine, 5-amino-2-chloropyridine, 2-amino-3-chloro-5-trifluoromethylpyridine, 6-amino-2,4-lutidine, 2-amino-3-picoline, etc.

When $R^3$ represents a quinolyl group:
2-aminoquinoline, 4-amino-2-methylquinoline, 5-amino-8-hydroxyquinoline, 8-amino-quinaldine, etc.

When $R^3$ represents an isoquinolyl group:
3-aminoisoquinoline, 4-aminoisoquinaline, etc.

When R represents an acridinyl group:
9-aminoacridine, 9-amino-1,2,3,4-tetrahydroacridine, etc.

When $R^3$ represents a triazinyl group:
3-amino-5,6-dimethyl-1,2,4-triazine, etc.

When $R^3$ represents an imidazolyl group:
5-aminoimidazole, 4-amino-5-carboethoxy-1-(4-methoxyphenyl)imidazole, etc.

When $R^3$ represents an pyrazolyl group:
5-amino-1-ethylpyrazole, 5-amino-1-phenylpyrazole, 5-amino-3-methyl-1-phenylpyrazole, 3-amino-5-methylpyrazole, 5-amino-3-methyl-1-p-tolylpyrazole, etc.

When R³ represents a triazolyl group:
1-aminobenzotriazole, 1-amino-4,5-diphenyltriazole, etc.
When R represents a tetrazolyl group:
5-aminotetrazole, 1-amino-5-butyltetrazole, etc.
When R³ represents a pyrimidyl group:
2-aminopyrimidine, 2-amino-4-chloro-6-methylpyrimidine, 2-amino-4,6-dichloropyrimidine, 2-amino-4,6-dihydroxypyrimidine, 2-amino-4,6-dimethoxypyrimidine, 2-amino-4-methyl-6-methoxypyrimidine, 2-amino-4,6-dimethylpyrimidine, etc.
When R³ represents a thiazolyl group:
2-aminothiazole, 2-amino-4,5-dimethylthiazole, 2-amino-5-nitrothiazole, etc.
When R³ represents an isothiazolyl group:
5-amino-3-methylisothiazole, 5-amino-4-bromo-3-methylisothiazole, etc.
When R³ represents a benzothiazolyl group:
2-aminobenzothiazole, 2-amino-6-methylbenzothiazole, 2-amino-6-methoxybenzothiazole, 2-amino-6-ethoxybenzothiazole, 2-amino-4-chlorobenzothiazole, 6-amino-2-mercaptobenzothiazole, etc.
When R³ represents a thiadiazolyl group:
2-amino-5-mercapto-1,3,4-thiadiazole, 2-amino-5-methyl-1,3,4-thiadiazole, etc.
When R³ represents a furanyl group:
2-aminofuran, methyl 5-amino-2-furoate, etc.
When R³ represents a benzofuranyl group:
3-aminodibenzofuran, 3-amino-2-methoxydibenzofuran, etc.
When R³ represents a cumarinyl group:
3-aminocumarin, 4-aminocumarin, 7-amino-4-methylcumarin, etc.
When R³ represents an isoxazolyl group:
5-aminoisoxazole, 5-amino-3-methylisoxazole, etc.
When R³ represents a benzoxazolyl group:
2-aminobenzoxazole, 2-amino-5-chlorobenzoxazole, etc.
In the formula (IV):

R⁴—NH—R⁵ (IV),

R⁴ and R⁵ respectively and independently from each other represent an alkyl group and preferably an alkyl group having 1 to 15 carbon atoms, for example, a methyl, ethyl, propyl or butyl group; an aralkyl group having 7 to 15 carbon atoms, for example, a benzyl or phenethyl group; an aryl group, preferably an aryl group having 6 to 14 carbon atoms, for example, a phenyl group; or a heterocyclic group, for example, a pyridyl group. Each of the alkyl, aralkyl, aryl, and heterocyclic groups may have at least one substituent selected from, for example, alkyl groups, aryl groups, alkoxy groups, aryloxy groups, halogen atoms, a nitro group and a cyano group. Also, R⁴ and R⁵ may be the same as each other or different from each other. When one of R⁴ and R⁵ is an aryl group, the other one is preferably not an aryl group. Also, R⁴ and R⁵ may be bonded to each other to form a cyclic structure.

The monoamine compounds represented by the formula (IV) include, for example, the following compounds.

The monoamine compounds in which both R⁴ and R⁵ represent the above-mentioned alkyl groups, include, for example, diisopropylamine, di-s-butylamine, di-2-amylamine, di-2-hexylamine, di-2-octylamine, N-t-butylisopropylamine, N-isopropyl-1,5-dimethylhexylamine, N-t-butylcyclohexylamine, dicyclopentylamine, dicyclohexylamine, dicycloheptylamine, 4,4'-dimethyldicyclohexylamine, etc.

The monoamine compounds in which both R⁴ and R⁵ represent the above-mentioned aralkyl groups include, for example, dibenzylamine, diphenethylamine, 4,4'-dimethyldibenzylamine, bis(2,4-dimethoxybenzyl)amine, N-benzyl-α-(3-methoxyphenyl)phenethylamine, dipiperonylamine, di-1-indanylamine, etc.

The monoamine compounds in which R⁴ and R⁵ represent the above-mentioned alkyl groups and aralkyl groups respectively include, for example, N-benzylmethylamine, N-benzylethylamine, N-benzylisopropylamine, N-benzyl-t-butylamine, N-benzylcyclopropylamine, N-(2-chloroethyl)benzylamine, 3-benzylaminopropionitrile, N-(4-chlorobenzyl)methylamine, N-ethyl-4-methoxybenzylamine, N-isopropyl-2-chloro-6-fluorobenzylamine, N-(3-methoxypropyl)-3,4,5-trimethoxybenzylamine, N-cyclopropylveratrylamine, 1,2-diphenylethyl-N-methylamine, α-(3,4-dimethoxyphenyl)-N-methylphenethylamine, etc.

The monoamine compounds in which R⁴ and R⁵ represent the above-mentioned alkyl groups and the aryl groups, respectively, include, for example, N-methylaniline, N-ethylaniline, N-propylaniline, N-butylaniline, N-cyclohexylaniline, N-allylaniline, N-ethyl-3-toluidine, N-ethyl-2,3-xylidine, N-methyl-4-anisidine, 3,4-methylenedioxy-N-ethylaniline, N-methyl-4-chloroaniline, N-methyl-4-fluoroaniline, N-ethylnaphthylamine, etc.

The monoamine compounds of which R⁴ and R⁵ represent the above-mentioned aralkyl groups and aryl groups, respectively, include, for example, N-benzylaniline, N-benzyl-3-trifluoromethylaniline, N-(4-fluorophenyl)-4-methoxybenzylaniline, N-(4-bromophenyl)veratrylamine, N-(4-chlorophenyl)-4-methylbenzylamine, etc.

The monoamine compounds of which R⁴ and R⁵ are bonded to each other to form a cyclic structure include, for example, 3,5-dimethylmorpholine, 2,5-dimethylpyrrolidine, 2,6-dimethylpyrrolidine, 6,7-dimetoxy-1,2,3,4-tetrahydroisoquinoline, 1,2,3,4-tetrahydroisoquinoline, 1,2,3,4-tetrahydroquinoline, benzothiazoline, 2,3-dihydroindole, 2-t-butyl-3-(4-chlorophenyl)aziridine, etc. These nitrogen-containing heterocyclic compounds have one hydrogen atom attached to the N-position thereof.

In the formula (V):

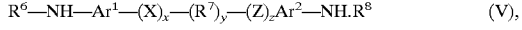

R⁶—NH—Ar¹—(X)ₓ—(R⁷)ᵧ—(Z)_z-Ar²—NH.R⁸ (V),

R⁶ and R⁸ respectively and independently from each other represent an alkyl group, preferably an alkyl group having 1 to 4 carbon atoms, for example, a methyl, ethyl, butyl or propyl group, or an aralkyl group, preferably an aralkyl group having 7 to 14 carbon atoms, for example, a benzyl group; Ar¹ and Ar² respectively and independently from each other represent an arylene group, preferably an arylene group having 6 to 12 carbon atoms, for example, a phenylene group or a naphthylene group;

R⁷ represents an alkylene group, preferably an alkylene group having 1 to 12 carbon atoms, for example, a methylene, ethylene, tetramethylene, or hexamethylene group, an alkenylene group, preferably an alkenylene group having 2 to 4 carbon atoms, for example, a vinylene group, an aralkylene group, preferably an aralkylene group having 7 to 13 carbon atoms, for example, a xylylene or phenethylene group, or an arylene group, preferably an arylene group having 6 to 12 carbon atoms, for example, a phenylene, naphthylene or biphenylene group; X and Z respectively and independently from each other represent a divalent group selected from alkylene groups, preferably alkylene groups having 1 to 4 carbon atoms, for example, methylene, ethylene, or tetramethylene groups and groups represented by —NH—, —O—, —S—, —SS—, —SO$_2$— and —CO—; and x, y and z respectively and independently from each other represent 0 or 1.

Each of the groups represented by $R^6$, $R^7$, $R^8$, $Ar^1$ and $Ar^2$ include isomers and may be substituted by at least one substituent selected from alkyl groups having 1 to 4 carbon atoms, alkoxy groups having 1 to 4 carbon atoms, acyl groups having 2 to 12 carbon atoms, aryl groups having 6 to 12 carbon atoms, aryloxy groups having 6 to 12 carbon atoms, halogen atoms, a nitro group, a cyano group and an amino group. Also, $Ar^1$ and $Ar^2$ may be directly bonded to each other when x=y=z=0, or may be cross-linked to each other through a divalent cross-linking group, preferably selected from alkylene groups with 1 to 2 carbon atoms, and —NH—, —O—, —S—, —SO$_2$—, —CO— and —CONH— groups.

The amine compounds represented by the formula (V) include, for example, the following compounds.

When $Ar^1$ and $Ar^2$ are directly bonded to each other (x=y=z=0):

benzidine, 3-methylbenzidine, o-tolidine, m-tolidine, 3,3'-diethylbenzidine, 3,3'-5,5'-tetramethylbenzidine, 3,3'-dimethoxybenzidine, 3,3'-dichlorobenzidine, 2,2',5,5'-tetrachlorobenzidine, 4,4'-diaminooctafluorobenzidine, 2-nitrobenzidine, naphthidine, 3,3'-dimethylnaphthidine, etc.

When $Ar^1$ and $Ar^2$ are bonded to each other through an alkylene or aralkylene group:

3,4'-diaminodiphenylmethane, 4,4'-diaminodiphenylmethane, 4,4'-diamino-2,2'-dimethyldiphenylmethane, 4,4'-(hexafluoroisopropylidene)dianiline, 4,4'-diaminodiphenyl-1,1-cyclohexane, 4,4'-bismethylaminodiphenylmethane, 4,4'-diamino-3,3'-dimethyldiphenyl-1,1-cyclohexane, 1,1-bis(4-amino-3-methoxyphenyl)cyclohexane, 4,4'-diaminotriphenylmethane, 4,4'-diamino-3,3'-dimethoxytriphenylmethane, 4,4'-diamino-3,3',5,5'-tetramethyldiphenylmethane, 4,4'-diamino-3,3'-dichlorodiphenylmethane, 4,4'-ethylenedianiline, 2,2'-ethylenedianiline, 4,4'-diamino-2,2'-dimethyldibenzyl, 2,2'-diamino-4,4'-difluorodibenzyl, etc.

When $Ar^1$ and $Ar^2$ are bonded to each other through an alkenylene group:

4,4'-diaminostilben, etc.

When $Ar^1$ and $Ar^2$ are bonded to each other through an arylene group:

4,4'-diamino-4-terphenyl, etc.

When X and/or Z is an —O— group:

4,4'-diaminodiphenylether, 3,4'-diaminodiphenylether, 4,4'-diamino-2,2'-dimethyldiphenylether, 1,4-bis(4-aminophenoxy)benzene, 1,3-bis(4-aminophenoxy)benzene, 1,3-bis(3-aminophenoxy)benzene, 4,4'-bis(4-aminophenoxy)biphenyl, 2,2-bis[4-(4-aminophenoxy)phenyl]propane, 2,2-bis[4-(4-aminophenoxy)phenyl]hexafluoropropane, 3,3'-(ethylenedioxy)dianiline, 4,4'-(trimethylenedioxy)dianiline, 3,3'-(tetramethylenedioxy)dianiline, 3,3'-(pentamethylenedioxy)dianiline, etc.

When $Ar^1$ and $Ar^2$ are bonded to each other through a —S— group, an —SS— group, or a —SO$_2$— group:

4,4'-diaminodiphenylsulfide, 2,2'-diaminodiphenyldisulfide, 4,4'-diaminodiphenyldisulfide, 2,2'-diamino-4,4'-dichlorodiphenyldisulfide, 2,2'-dithiobis(1-naphthylamine), 3,3'-bis(aminophenyl)sulfone, 4,4'-diaminodiphenylsulfone, o-tolyldisulfone, bis[4-(4-aminophenoxy)phenyl]sulfone, etc.

When $Ar^1$ and $Ar^2$ are bonded to each other through a —CO— group:

3,3'-diaminobenzophenone, 4,4'-diaminobenzophenone, etc.

When $Ar^1$ and $Ar^2$ are bonded to each other through a —CO—NH— group:

4,4'-diaminobenzanilide, etc.

When $Ar^1$ and $Ar^2$ are directly bonded to each other and simultaneously cross-linked through the above-mentioned divalent cross-linking groups:

o-tolidinesulfone, 2,7-diaminofluorene, 3,7-diamino-2-methoxyfluorene, 3,8-diamino-6(5H)-phenanthridine, etc.

Also, the amine compounds of the formula (V) may be polyamine compounds, for example, polymethylenepolyphenylenepolyamines, produced by reacting aniline compounds with formaldehyde in the presence of an aqueous acid solution.

In the formula (VI):

$$R^9\text{—NH—}R^{10}\text{—NH—}R^1 \qquad (VI),$$

$R^9$ and $R^{11}$ represents a hydrogen atom, an alkyl group preferably having 1 to 10 carbon atoms, for example, a methyl, ethyl, propyl or butyl group, an aralkyl preferably having 7 to 14 carbon atoms, for example, a benzyl group, or an aryl group preferably having 6 to 14 carbon atoms, for example, a phenyl, tolyl, or xylyl group, and $R^{10}$ represents an alkylene group preferably having 1 to 12 carbon atoms, for example, a methylene, ethylene, tetramethylene or hexamethylene group, or an aralkyl group preferably having 8 to 16 carbon atoms, for example, a xylylene or phenethylene group, an arylene group having 6 to 16 carbon atoms, for example, a phenylene, naphthylene or biphenylene group.

When $R^{10}$ is an arylene group, the two amino groups are preferably attached to one and the same aromatic ring, and in this case, $R^9$ and $R^{11}$ preferably represent an alkyl or aralkyl group.

The groups represented by each of $R^9$, $R^{10}$ and $R^{11}$ include isomers thereof and each of these groups may have one or more substituents selected from alkyl groups with 1 to 4 carbon atoms, alkoxy groups with 1 to 4 carbon atoms, acyl groups with 2 to 12 carbon atoms, aryl groups with 6 to 12 carbon atoms, aryloxy groups with 6 to 12 carbon atoms, halogen atoms, a nitro group, a cyano group, and an amino group.

The amine compounds represented by the formula (VI) include, for example, the following compounds.

When $R^{10}$ represents an arylene group:

m-phenylenediamine, p-phenylenediamine, 1,5-diaminonaphthalene, 1,8-diaminonaphthalene, 2,3-diaminonaphthalene, 2,7-diaminonaphthalene, 2,4-diaminotoluene, 2,5-diaminotoluene, 2,6-diaminotoluene, 2,4-diamino-3,5-diethyltoluene, 4,6-diamino-2,5-diethyltoluene, 4-isopropyl-1,3-phenylenediamine, 5-trifluoromethyl-1,3-phenylenediamine, 2,4,6-trimethyl-1,3-phenylenediamine, 2,3-dimethyl-1,4-phenylenediamine, 2,5-dimethyl-1,4-phenylenediamine, 2,3,5,6-tetramethyl-1,3-phenylenediamine, 2,6-diamino-4-nitrotoluene, 5-nitro-1,3-phenylenediamine, nitro-1,4- phenylenediamine, 2-ethoxy-1,3-phenylenediamine, 4-ethoxy-1,3-phenylenediamine, 4-methoxy-1,3-phenylenediamine, 2-methoxy-5-benzyl-1,4-phenylenediamine, 4-chloro-1,3-phenylenediamine, 5-chloro-1,3-phenylenediamine, 5-fluoro-1,3-phenylenediamine, 2,4,5,6-tetrafluoro-1,3-phenylenediamine, 2,5-dichloro-1,4-phenylenediamine, chloro-1,4-phenylenediamine, tetrafluoro-1,4-phenylenediamine, 3-(methylamino)aniline, N-methyl-1,4-phenylenediamine, N,N'-di-sec-butyl-1,4-phenylenediamine, N,N'-diisopropyl-1,4-phenylenediamine, N,N'-dihexyl-1,4-phenylenediamine, N,N'-dibenzyl-1,4-phenylenediamine, cyano-1,4-phenylenediamine, etc.

When $R^{10}$ represents an aralkylene group:
m-xylylenediamine, p-xylylenediamine, α,α'-bis(4-iodoanilino)-p-xylene, α,α'-bis(4-ethylanilino)-p-xylene, 2,3,5,6-tetrachloro-p-xylylenediamine, 2,4,5,6-tetrachloro-m-xylylenediamine, etc.

When $R^{10}$ represents an alkylene group:
N,N'-bis(phenylmethyl)-1,6-hexanediamine, N,N'-diphenyl-1,6-hexanediamine, etc.

In the amine compound (piperazine compounds) represented by the formula (VII):

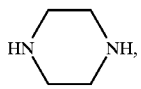

(VII)

the carbon atoms from which the piperazine ring is formed may be substituted with at least one substituted selected from, for example, alkyl groups with 1 to 4 carbon atoms, alkoxy groups with 1 to 4 carbon atoms, acyl groups with 2 to 12 carbon atoms, aryl groups with 6 to 12 carbon atoms, aryloxy groups with 6 to 12 carbon atoms, halogen atoms, a nitro group, a cyano group, an amino group, etc.

The amine compounds represented by the general formula (VII) include, for example, piperazine, 2-methylpiperazine, 2,5-dimethylpiperazine, 2,6-dimethylpiperazine, 2,3,5,6-tetramethylpiperazine, 1,2,3,4-tetrahydroquinoxaline, etc.

In the process of the present invention, the reaction between a diaryl carbonate with an amine compound having one or more hydrogen atoms attached to N-position is carried out in the presence of at least one carboxylic acid selected from those of the formulae (I) and (II):

$R^1$—COOH (I)

and $R^2$—COOH (II).

In the formula (I): $R^1$—COOH, $R^1$ represents a member selected the group consisting of:

(1) alkyl groups and cycloalkyl groups each having an α-positioned carbon atom bonded to the —COOH group and to only one hydrogen atom, preferably alkyl groups having 3 to 15 carbon atoms and cycloalkyl groups having 5 to 15 carbon atoms, for example, isopropyl, secondary butyl group and cyclohexyl group;

(2) alkyl groups having an α-positioned carbon atom bonded to the —COOH group and to no hydrogen atom, which alkyl groups may include a cycloalkyl structure, preferably alkyl groups having 4 to 16 carbon atoms, for example, tert-butyl, and 1-methylcyclohexyl groups;

(3) aryl groups, for example, phenyl and naphthyl groups; and (4) heterocyclic groups, for example, furyl, thienyl and pyridyl groups.

The carboxylic acids represented by the formula (I) and usable for the present invention include, for example, the compounds as shown below.

(a) The carboxylic acids of the formula (I) in which $R^1$ represents the alkyl groups shown in the above mentioned group (1) and which have 4 to 16 carbon atoms:
Isobutyric acid, 2-methylbutyric acid, etc.

(b) The carboxylic acids of the formula (I) in which $R^1$ represents the alkyl groups shown in the above-mentioned group (2), and which have 5 to 17 carbon atoms:
pivalic acid, triethylacetic acid, 2,2-dimethylbutyric acid.

(c) The carboxylic acids (cycloalkane carboxylic acids) of the formula (I) in which $R^1$ represents the cycloalkyl groups as shown in the above-mentioned group (1) or the cycloalkyl structure-containing alkyl group as shown in the above-mentioned group (2), and which have 6 to 16 carbon atoms:
cyclopentane carboxylic acid, cyclohexane carboxylic acid, 1-methylcyclohexane carboxylic acid, decalin carboxylic acid, 1-adamantane carboxylic acid, etc.

(d) The aromatic carboxylic acids in which $R^1$ represents aryl groups and which have 7 to 17 carbon atoms:
benzoic acid, fluorobenzoic acid chlorobenzoic acid, dichlorobenzoic acid, toluic acid, anisic acid, salicylic acid, naphthalenecarboxylic acid, anthracenecarboxylic acid, phthalic acid, isophthalic acid, terephthalic acid, etc.

(e) The heterocyclic carboxylic acids in which $R^1$ represents heterocyclic groups and which have 5 to 16 carbon atoms:
furancarboxylic acid, thiophenecarboxylic acid, pyridinecarboxylic acid, pyrrolecarboxylic acid, etc.

The carboxylic acids of the formula (I) are preferably selected from aliphatic carboxylic acids in which $R^1$ represents alkyl groups having an α-positioned carbon atom bonded to the —COOH group and to no hydrogen atom and which have 5 to 16 carbon atoms; cycloaliphatic carboxylic acids in which $R^1$ represents cycloalkyl groups having an α-positioned carbon atom bonded to the —COOH group and to no hydrogen atom, and which have 6 to 16 carbon atoms; aromatic carboxylic acids in which $R^1$ represents aryl groups and which have 7 to 17 carbon atoms; and heterocyclic carboxylic acids in which $R^1$ represents heterocyclic groups and which have 5 to 16 carbon atoms.

In the formula (II):

$R^2$—COOH (II), $R^2$ represents (5) alkyl groups having an α-positioned carbon atom bonded to the —COOH group and at least two hydrogen atoms, the alkyl groups having 1 to 15 carbon atoms.

The carboxylic acids of the formula (II) are preferably selected from aliphatic carboxylic acids having 2 to 16 carbon atoms, for example, acetic acid, propionic acid, butyric acid, valeric acid and isovaleric acid.

The carboxylic acids of the formula (II) are employed in a feeding concentration of 0.005 mole/liter or more in the reaction of the process of the present invention.

In the process of the present invention, the reaction of the diaryl carbonate with the amine compound in the presence of the carboxylic acid is carried out, for example, by feeding the diaryl carbonate, the amine compound and the carboxylic acid each in a necessary amount into a reactor, and optionally adding a reaction medium to the reaction mixture.

In this reaction, the reaction temperature is variable in response to the types of the material compounds and the reaction medium, and is preferably in the range from −30° C. to 200° C., more preferably −5° C. to 150° C., because when the reaction temperature is too high, various undesirable urea derivatives may be produced as by-products. The reaction pressure may be the ambient atmospheric pressure, an increased pressure or a reduced pressure, and thus there is no specific limitation to the reaction pressure. Preferably, the reaction is carried out while stirring the reaction mixture. However, the stirring is not always necessary. When the reaction mixture liquid is solidified during the reaction, the reaction medium is preferably used to enhance the operational efficiency of the reaction.

The reaction medium usable for the reaction of the process of the present invention is not limited to specific groups of compounds, as long as the reaction medium is non-reactive or scantly reactive to the diaryl carbonate and the amine compounds used as starting materials, to the resultant carbamate produced as a reaction product and to the carboxylic acid.

The reaction medium is preferably used, for example, in an amount of 50 parts by weight or less, more preferably 20 parts by weight or less, still more preferably 10 parts by weight or less, per part by weight of the diaryl carbonate. In the case where an aromatic amine or secondary amine is used as an amine compound, the reaction medium is preferably employed in an amount of, for example, 10 parts by weight or less, more preferably 5 parts by weight or less, per part by weight of the diaryl carbonate. Also, the reaction medium may consist of only one compound or of a mixture of two or more compounds.

As a reaction medium usable for the reaction of the process of the present invention, for example, aliphatic alcohol compounds (for example, methyl alcohol, ethyl alcohol, n-propyl alcohol, isopropyl alcohol, n-butyl alcohol, isobutyl alcohol, etc.); aliphatic hydrocarbons (for example, hexane, pentane, heptane, octane, petroleum ether, ligroin, mineral oil, cyclopentane, cyclohexane, cyclooctane, cyclododecane, and decalin); aromatic hydrocarbons and halogenated aromatic hydrocarbons (for example, benzene, toluene, xylene, ethylbenzene, isopropylbenzene, diisopropylbenzene, tetralin, butyl benzene, cyclohexylbenzene, tetralin, chlorobenzene, o-dichlorobenzene, methylnaphthalene, chloronaphthalene, etc.); ethers (for example, diethylether, diisopropylether, dibutylether, anisole, diphenylether, tetrahydrofuran, dioxane, ethyleneglycoldimethylether, ethyleneglycoldiethylether, ethyleneglycoldibutylether, diethyleneglycoldimethylether, etc.); nitriles (for example, acetonitrile, propionitrile, adiponitrile, benzonitrile, etc.); aliphatic halogenated hydrocarbons (for example, methylene chloride, chloroform, 1,2-dichloroethane, 1,2-dichloropropane, 1,4-dichlorobutane, etc.), amides (for example, N,N-dimethylformamide, N,N-dimethylacetamide, etc.); nitro compounds (for example, nitromethane, nitrobenzene, etc.); phenol compounds (for example, phenol, cresole, xylenol, nitrophenol, chlorophenol, catechol, naphthol, etc.); and N-methylpyrrolidinone, N,N-dimethylimidazolidinone, and dimethylsulfoxide.

Among the above-mentioned compounds for the reaction medium, the aliphatic hydrocarbons, aromatic hydrocarbons, ethers, aliphatic halogenated hydrocarbons, and/or nitro compounds are preferably used, and the aliphatic hydrocarbons, aromatic hydrocarbons and nitro compounds are more preferably used and, particularly, the aliphatic hydrocarbons and/or aromatic hydrocarbons are still more preferably used. When the aliphatic hydrocarbons and aromatic hydrocarbons are used as a reaction medium and since, after the reaction is completed, the resultant carbamate precipitates from the reaction liquid, the carbamate with a high degree of purity can be very easily isolated.

In an embodiment (1) of the process of the present invention, preferably the carboxylic acid of the formula (I) is used in a feeding molar amount of 0.005 to 5 times the feeding molar amount of the diaryl carbonate, and at least one amine compound selected from the amine compounds of the formulae (III) to (IV) is employed in a feeding molar amount of 0.05 to 20 times the feeding amount of the diaryl carbonate.

In the above-mentioned embodiment (1), more preferably the feeding molar amount of the carboxylic acid of the formula (I) is 0.01 to 2 times, still more preferably 0.02 to 1.5 times, the feeding molar amount of the diaryl carbonate. The feeding weight amount of the carboxylic acid of the formula (I) is preferably 0.05 to 70%, more preferably 0.2 to 50%, by weight based on the total weight amount of the reaction liquid. Also, the carboxylic acids of the formula (I) may be employed alone or in a mixture of two or more thereof, and may be in the form of a salt thereof with the amine compounds.

The amine compounds of the formulae (III) and/or (IV) is preferably used in a feeding molar amount of 0.3 to 3 times, more preferably 0.5 to 2 times, the feeding molar amount of the diaryl carbonate.

In this embodiment, the reaction temperature is −30° C. to 200° C., preferably −5° C. to 150° C. There is no limitation to the reaction pressure. Also, the above-mentioned reaction medium may be used for the embodiment.

In another embodiment (2) of the process of the present invention, at least one amine compounds selected from those of the formulae (V) to (VII) is used, and the carboxylic acid is used in a feeding molar amount of 0.001 to 5 times the feeding molar amount of the amine compound.

In the embodiment (2), the amine compound is preferably used in a molar amount of 0.5 mole or less, more preferably 0.01 to 0.5 mole, still more preferably 0.05 to 0.5 mole, per mole of the diaryl carbonate.

The carboxylic acid as mentioned above is preferably used in a feeding molar amount of 0.001 to 5 moles, more preferably 0.001 to 2 moles, still more preferably 0.02 to 2 moles, per mole of the amine compound. Most preferably, the carboxylic acid is used in an amount of 0.02 to 1.5 moles per mole of the amine compound.

The carboxylic acids are selected from those of the formulae (I) and (II) and may be used alone or in a mixture of two or more thereof. The carboxylic acids can be used in the form of a salt thereof with the amine compounds. Usually, the carboxylic acid is preferably selected from those of the formula (I).

Also, the reaction medium is preferably employed in an amount of 50 parts by weight or less, more preferably 20 parts by weight or less, still more preferably 10 parts by weight or less, per part by weight of the amine compound.

In the reaction of the embodiment (2), preferably, the reaction temperature is 0 to 200° C., more preferably 10 to 150° C., there is no limitation to the reaction pressure, the reaction medium may be used or may not be used, and there is no limitation to the type of the reaction medium.

In still another embodiment (3) of the process of the present invention, the carboxylic acid of the formula (II) is used in a feeding concentration of 0.005 mole/liter or more, at least one amine compound selected from those of the formulae (III) and (IV) is used in a feeding concentration of 0.5 mole/liter or more, and the diaryl carbonate is used in a feeding concentration of 0.5 mole/liter or more.

In this embodiment (3), the feeding concentration of the diaryl carbonate is 0.5 mole/liter or more, preferably 0.5 to 4.9 mole/liter, still more preferably 0.6 to 4.5 mole/liter. Particularly, when the diaryl carbonate has no electron-attractive aryl group, the feeding concentration of the diaryl carbonate is preferably 0.7 mole/liter or more, more preferably 0.8 to 4.5 mole/liter. The reaction rate of the diaryl carbonate with the amine compound decreases with a decrease in the feeding concentration of the diaryl carbonate.

In the embodiment (3), the feeding concentration of the amine compound of the formulae (III) and/or (IV) is 0.5 mole/liter or more, preferably 0.5 to 9.5 mole/liter, still more preferably 0.6 to 9.0 mole/liter. Particularly, when the diaryl carbonate has no electron-attractive aryl group, the amine compound is preferably used in a feeding concentration of 0.7 mole/liter or more, more preferably 0.7 to 9.5 mole/liter, still more preferably 0.8 to 9.0 mole/liter. The reaction rate of the amine compound with the diaryl carbonate decreases with a decrease in the feeding concentration of the amine compound.

In the embodiment (3), the feeding molar amount of the amine compounds of the formulae (III) and/or (IV) is preferably 0.1 to 19 times, more preferably 0.3 to 3 times, still more preferably 0.5 to 2 times, the feeding molar amount of the diaryl carbonate.

In the embodiment (3), the feeding concentration of the carboxylic acid of the formula (II) is 0.005 mole/liter or more, more preferably 0.005 to 14 mole/liter, still more preferably 0.08 to 14 mole/liter.

Also, the feeding molar amount of the carboxylic acid of the formula (II) is preferably 0.002 to 28 times, more preferably 0.005 to 5 times, still more preferably 0.01 to 1.5 times, the feeding molar amount of the diaryl carbonate.

The reaction medium usable for the reaction of the embodiment (3) is not limited to specific type of compound, as long as the reaction medium is non-reactive or scantly reactive to the starting materials, namely diaryl carbonates and amine compounds, the reaction product, namely carbamates, and the carboxylic acid of the formula (II). However, the reaction medium is used in an amount within a range in which the above-mentioned feeding concentrations of the diaryl carbonate, amine compound and carboxylic acid can be satisfied.

The reaction medium is preferably used in an amount of 6.8 parts by weight or less, more preferably 6.0 parts by weight or less, still more preferably 5 parts by weight or less, per part by weight of the feeding amount of the diaryl carbonate.

In the embodiment (3) as mentioned above, the reaction temperature is variable in response to the types of the material compounds and the reaction medium, and is usually 10 to 200° C., preferably 15 to 150° C. The reaction pressure is not limited to a specific level and may be the ambient atmospheric pressure, an increased pressure or a reduced pressure. Also, the reaction procedure is preferably carried out while stirring. However, the stirring is not always necessary. The reaction medium is employed to enhance the efficiency of the reaction procedure when the reaction liquid is solidified as a whole.

In the embodiment (3) as mentioned above, preferably, the feeding concentration of the carboxylic acid of the formula (II) is 0.005 to 14 mole/liter, the feeding concentration of at least one amine compound selected from those of the formulae (III) and (IV) is 0.5 to 9.5 mole/liter, and the feeding concentration of the diaryl carbonate is 0.5 to 4.9 mole/liter.

In the process of the present invention, after the reaction is completed, the target aryl carbamate is isolated and collected from the reaction mixture containing the aryl carbamate. In this isolating step, when the reaction medium is present, the temperature of the reaction mixture is controlled to 40° C. or less, preferably 40° C. to −30° C., more preferably 30° C. to −25° C., to precipitate the aryl carbamate from the reaction mixture, and the precipitated aryl carbamate is isolated and collected by filtration or centrifugal separation. The temperature for precipitating the aryl carbamate from the reaction mixture is variable in response to the types of the material compounds, the resultant products and the reaction medium, and usually is 40° C. or less but not less than the temperature at which the reaction medium is solidified. When the reaction temperature is within the above-mentioned range of the precipitation temperature, after the reaction is completed, the aryl carbamate is precipitated from the reaction mixture, and thus the precipitated aryl carbamate can be isolated and collected from the reaction mixture without maintaining the temperature of the reaction mixture within the above-mentioned temperature range. When the reaction medium is not employed in the reaction step, preferably the resultant reaction mixture is added with a reaction medium scantly soluble in water, and then the same precipitation procedure as mentioned above is applied to the reaction mixture.

In some types of carboxylic acid, an amine salt of the carboxylic acid may be precipitated together with the carbamate. The amine salt can be easily removed from the carbamate by washing the crystals of the amine salt with water. Also, in the case where the amine salt of the carboxylic acid is more easily precipitated than the aryl carbamate, the precipitated amine salt is separated in the state of a solid before the aryl carbamate precipitates, or a mixture of the crystals of the amine salt and the aryl carbamate is treated with an organic solvent to extract and collect the aryl carbamate from the mixture.

In the process of the present invention, to isolate and collect the aryl carbamate from the reaction mixture liquid containing the reaction products produced by the reaction, by other procedures, after the reaction is completed and non-reacted amine compound is removed from the reaction mixture, the carbamate is isolated and collected. This method is advantageous when the precipitation of the carbamate in the form of crystals from the reaction mixture is difficult.

The non-reacted amine compound in the reaction mixture is preferably removed by treating the reaction mixture with an aqueous solution containing an acid in an excessive amount with respect to the amount of the non-reactive amine compound (namely, of 1 to 30 times, preferably 1 to 10 times the molar amount of the non-reacted amine compound), to extract and remove the non-amine compound into the aqueous solution. In this case, there is no limitation to the acid, and, for example, an inorganic acid such as hydrochloric acid or sulfuric acid can be advantageously used. In the reaction step of the process of the present invention, when no reaction medium is used, the non-reacted amine compound is preferably removed by adding a reaction medium scantily soluble in water to the reaction mixture, and then treating the mixture in the same manner as mentioned above.

After the non-reacted amine compound is removed, a relevant after-treatment is applied to the resultant reaction mixture, to isolate and collect the aryl carbamate. For example, the reaction medium, the carboxylic acid and the phenol compound are removed from the reaction mixture by distillation, and the remaining solid substance is directly collected, or the solid substance is washed with a solvent, or recrystallized, to isolate and collect the aryl carbamate. Alternatively, the reaction mixture is treated with an aqueous alkali solution to remove the carboxylic acid and phenol compound from the reaction mixture, (and optionally the phenol compound is removed by distillation), and then the reaction medium is removed by distillation and the remaining solid substance is directly isolated and collected. Further alternatively, the solid substance is washed with a solvent or subjected to recrystallization to isolate and collect the aryl carbamate.

In the method of isolating and collecting the aryl carbamate by precipitating the aryl carbamate from the reaction mixture, after the aryl carbamate is isolated and collected, the remaining mother liquid can be subjected to the above-mentioned alkali treatment to advantageously recover the aryl carbamate remaining in the mother liquid.

The solvent usable for the above-mentioned recrystallization includes, for example, aliphatic hydrocarbons (for example, pentane, hexane, petroleum ether, ligroin, cyclohexane, cyclododecane, decaline, etc.); aromatic hydrocarbons and halogenated aromatic hydrocarbons (for example, benzene, toluene, xylene, ethyl benzene, isopropylbenzene, n-butylbenzene, tetralin, chlorobenzene, etc.); aliphatic alcohols (for example, ethyl alcohol, isopropyl alcohol, n-butyl alcohol, isoamyl alcohol, cyclohexyl alcohol, etc.); ethers (for example, di-n-propylether, diisopropylether, di-n-butylether, etc.); esters (for example, ethyl acetate, isopropyl acetate, n-butyl acetate, isobutyl acetate, n-amyl acetate, isoamyl acetate, cyclohexyl acetate, etc.); ketones (for example, methylisobutylketone, diisobutylketone, cyclohexanone, etc.).

The aryl carbamate collected by the above-mentioned procedures has a high degree of purity. If necessary, the aryl carbamate is further refined by applying recrystallization, distillation, sublimation, or column chromatography.

In the case where the aryl carbamate produced by the reaction of the process of the present invention is scantly soluble in the reaction medium, and the diaryl carbonate, the amine compound, the carboxylic acid and phenol compounds produced as by-products are easy soluble in the reaction medium, after the reaction is completed, the resultant aryl carbamate having a high degree of purity can be isolated and collected only by filtration or centrifugal separation of the reaction mixture.

In this case, after the filtration or centrifugal separation, the mother liquid may be reused for the reaction of the process of the present invention, by, after optionally removing the phenol compounds produced as by-products and the reaction medium from the mother liquid, adding the diaryl carbonate, amine compounds and carboxylic acid in the necessary amounts to the mother liquid.

The present invention will be further explained in detail by the following examples and comparative examples.

In the examples, the selectivity and yield of aryl carbamate were calculated based on molar amount thereof with respect to the conversion and feeding amount of diaryl carbonate. The yield of acid amide was calculated based on molar amount thereof with respect to the feeding amount of carboxylic acid.

REFERENCE EXAMPLE 1

[Synthesis of bis(3,5-dimethoxyphenyl)carbonate]

A glass flask equipped with a distillator and having an inside volume of 20 ml was charged with a mixture of 0.02 mole of diphenyl carbonate, 0.04 mole of 3,5-dimethoxyphenol and 0.0002 mole of titanium tetraphenoxide, the mixture was stirred at a bath temperature of 175 to 190° C. under a pressure of 3999.6 to 2666.4 Pa (30 to 20 mmHg) for 2 hours. Then, the mixture was added with 0.013 mole of 3,5-dimethoxyphenol, the resultant mixture was stirred at 190° C. under 2666.4 to 1333.2 Pa (20 to 10 mmHg) for 2 hours. Phenol produced during the reaction was distilled and removed by the distillor.

After the reaction was completed, the reaction mixture liquid was cooled to room temperature, mixed with methylene chloride and water to extract the reaction product into methylene chloride. Then, the resultant methylene chloride phase was dried on anhydrous magnesium sulfate, and methylene chloride was removed by distillation, and the remaining 3,5-dimethoxyphenol was removed by distillation. The resultant distillation residue was refined by silica gel column chromatography, and the resultant solid substance was recrystallized from diisopropylether. Bis(3,5-dimethoxyphenyl)carbonate in the form of white crystals was obtained at a yield of 83.6%. The white crystals had a melting temperature of 82° C. The IR spectrum of the white crystals had an absorption at 1774 $cm^{-1}$. The elemental analysis result of the white crystals was consistent with the theoretical values thereof.

EXAMPLE 1

A glass reactor equipped with a reflux condenser and having an inside volume of 50 ml was charged with a mixture of 0.01 mole of diphenyl carbonate, 0.012 mole of aniline and 0.002 mole of pivalic acid. The mixture was heated and stirred at a bath temperature of 75° C. under the ambient atmospheric pressure for 4 hours.

After the reaction was completed, the reaction mixture liquid was analyzed by high performance liquid chromatography. It was confirmed that the selectivity of phenyl N-phenyl carbamate was 98.4%, and the yield thereof was 93.0%. Also, it was confirmed that the yield of 1,3-diphenylurea was 0.1% and no pivalic acid anilide was produced.

EXAMPLES 2 TO 7

In each of Examples 2 to 7, the same reaction procedures and analysis as in Example 1 were carried out, except that pivalic acid was replaced by 0.002 mole of the carboxylic acid as shown in Table 1, and the reaction temperature was changed as shown in Table 1.

The analysis results are shown in Table 1.

Also, it was confirmed that in each example, no carboxylic acid anilide was produced.

COMPARATIVE EXAMPLE 1

The same reaction procedure and analysis as in Example 1 were carried out except that no pivalic acid was added and the reaction was carried out at a bath temperature of 85° C. for 6 hours. In the reaction result, the yield of phenyl N-phenylcarbamate was 1.0% or less. The analysis results of Comparative Example 1 are shown in Table 1.

TABLE 1

| Example No. | Carboxylic acid | Reaction temperature (° C.) | Carbamate selectivity (%) | Carbamate yield (%) | Diphenylurea yield (%) |
|---|---|---|---|---|---|
| Example | | | | | |
| 1 | Pivalic acid | 75 | 98.4 | 93.0 | 0.1 |
| 2 | Isobutyric acid | 75 | 99.8 | 92.5 | 0.1 |
| 3 | Benzoic acid | 75 | 99.5 | 95.3 | 0.1 |
| 4 | o-Chlorobenzoic acid | 75 | 99.7 | 97.2 | 0.1 |
| 5 | Cyclohexanecarboxylic acid | 75 | 97.2 | 91.7 | 0.2 |
| 6 | 2-Furancarboxylic acid | 85 | 98.9 | 95.5 | 0.7 |
| 7 | 2-Thiophenecarboxylic acid | 75 | 99.6 | 95.7 | 0.3 |
| Comparative Example | | | | | |
| 1 | — | 85 | — | <1.0 | — |

Note:
Reaction time:
4 hours in Examples 1 to 7
6 hours in Comparative Example 1

EXAMPLE 8

The same reaction and analysis procedures as in Example 1 were carried out except that the pivalic acid was replaced by 0.002 mole of isobutyric acid, and the reaction temperature was changed to 85° C.

In the reaction result, the selectivity of phenyl N-phenylcarbamate was 99.4% and the yield thereof was 97.1%. Also, the yield of 1,3-diphenylurea was 0.5% and the yield of acid amide (anilide of isobutyric acid) was 0.21%.

The analysis results are shown in Table 2.

COMPARATIVE EXAMPLES 2 TO 4

In each of Comparative Examples 2 to 4, the same reaction and analysis procedures as in Example 8 were carried out except that isobutyric acid was replaced by 0.002 mole of the carboxylic acid as shown in Table 2.

The analysis results are shown in Table 2.

TABLE 2

| Example No. | Carboxylic acid | Carbamate selectivity (%) | Carbamate yield (%) | Diphenylurea yield (%) | Acid amide yield (%) |
|---|---|---|---|---|---|
| Example 8 | Isobutyric acid | 99.4 | 97.1 | 0.5 | 0.2 |
| Comparative Example | | | | | |
| 2 | Propionic acid | 99.4 | 96.3 | 0.6 | 1.3 |
| 3 | Acetic acid | 99.4 | 95.8 | 0.6 | 2.1 |
| 4 | Formic acid | 95.1 | 83.0 | 0.5 | 87.3 |

[Note]
Reaction temperature: 85° C.
Reaction time: 4 hours

EXAMPLES 9 TO 12

In each of Examples 9 to 12, the same reaction and analysis procedures as in Example 1 were carried out, except that the amount of pivalic acid was changed to that as shown in Table 3.

The analysis results are shown in Table 3.

TABLE 3

| Example No. | Amount[*]1 of pivalic acid | Carbamate selectivity (%) | Carbamate yield (%) | Diphenylurea yield (%) |
|---|---|---|---|---|
| Example | | | | |
| 9 | 2 | 99.1 | 81.8 | 0.2 |
| 10 | 5 | 98.7 | 86.0 | 0.2 |
| 11 | 10 | 98.5 | 91.1 | 0.2 |
| 1 | 20 | 98.4 | 93.0 | 0.1 |
| 12 | 50 | 99.6 | 97.3 | 0.2 |

[Note]
*1: The amount of pivalic acid was given by a relative molar amount to the feeding molar amount of 100 of diphenyl carbonate.
Reaction temperature: 75° C.
Reaction time: 4 hours

EXAMPLE 13 TO 20

In each of Examples 13 to 20, the same reaction and analysis procedures as in Example 1 were carried out, except that aniline was replaced by 0.012 mole of the monoamine compound as shown in Table 4, and the reaction temperature and the reaction time were changed to those as shown in Table 4.

The analysis results are shown in Table 4.

TABLE 4

| Example No. | Monoamine compound | Reaction temperature (° C.) | Reaction time (hr) | Carbamate selectivity (%) | Carbamate yield (%) |
|---|---|---|---|---|---|
| Example | | | | | |
| 13 | 4-Chloroaniline | 85 | 5 | 99.1 | 87.8 |
| 14 | 2-Chloroaniline | 120 | 6 | 98.3 | 82.3 |
| 15 | 4-toluidine | 90 | 2 | 98.9 | 83.8 |
| 16 | 2-Anisidine | 85 | 9 | 98.5 | 83.9 |
| 17 | 4-Anisidine | 85 | 2 | 99.0 | 84.1 |
| 18 | 2-Aminodiphenyl | 100 | 6 | 94.3 | 71.0 |
| 19 | 2-Aminodiphenylether | 100 | 6 | 97.8 | 73.3 |
| 20 | 2-Naphthylamine | 100 | 4 | 98.7 | 90.3 |

EXAMPLE 21

The same reaction and analysis procedures as in Example 1 were carried out with the following exceptions.

Aniline was replaced by 0.012 mole of 3-aminopyridine, the amount of pivalic acid was changed to 0.015 mole, and the reaction was carried out at a temperature of 40° C. for 6 hours. In the reaction result, the selectivity of phenyl N-3-pyridylcarbamate was 98.3% and the yield thereof was 41.9%.

The analysis results are shown in Table 5.

COMPARATIVE EXAMPLE 5

The same reaction and analysis procedures as in Example 21 were carried out except that no pivalic acid was added.

In the reaction result, the selectivity of phenyl N-3-pyridylcarbamate was 49.0% and the yield thereof was 2.4%.

The analysis results are shown in Table 5.

EXAMPLE 22

The same reaction and analysis procedures as in Example 1 were carried out with the following exceptions.

Aniline was replaced by 0.012 mole of benzylamine, 40 ml of a reaction medium consisting of methylene chloride were added, and the reaction was carried out at a temperature of 0° C. for one hour. In the reaction result, the selectivity of phenyl N-benzylcarbamate was 99.2% and the yield thereof was 44.0%.

The analysis results are shown in Table 5.

COMPARATIVE EXAMPLE 6

The same reaction and analysis procedures as in Example 22 were carried out except that no pivalic acid was added.

In the reaction result, the selectivity of phenyl N-benzylcarbamate was 99.0% and the yield thereof was 21.5%.

The analysis results are shown in Table 5.

EXAMPLE 24

The same reaction and analysis procedures as in Example 1 were carried out with the following exceptions.

Aniline was replaced by 0.012 mole of dibenzylamine, a reaction medium, consisting of toluene was added in an amount of 4 ml and the reaction was carried out at a temperature of 90° C. for 6 hours. In the reaction result, the selectivity of phenyl N,N-dibenzylcarbamate was 98.5% and the yield thereof was 96.1%.

The analysis results are shown in Table 6.

COMPARATIVE EXAMPLE 7

The same reaction and analysis procedures as in Example 23 were carried out except that no pivalic acid was added.

In the reaction result, the selectivity of phenyl N,N-dibenzylcarbamate was 78.5% and the yield thereof was 8.3%.

The analysis results are shown in Table 6.

EXAMPLE 25

The same reaction and analysis procedures as in Example 1 were carried out with the following exceptions.

Aniline was replaced by 0.012 mole of dicyclohexylamine, a reaction medium consisting of anisole was added in an amount of 0.4 ml, and the reaction was carried out at a temperature of 150° C. for 5 hours. In the

TABLE 5

| | | Item | | | |
|---|---|---|---|---|---|
| Example No. | Monoamine compound | Amount(*)2 of pivalic acid | Reaction temperature (° C.) | Reaction time (hr) | Carbamate selectivity (%) | Carbamate yield (%) |
| Example 21 | 3-Aminopyridine | 150 | 40 | 6 | 98.3 | 41.9 |
| Comparative Example 5 | 3-Aminopyridine | 0 | 40 | 6 | 49.0 | 2.4 |
| Example 22 | Benzylamine | 20 | 0 | 1 | 99.2 | 44.0 |
| Comparative Example 6 | Benzylamine | 0 | 0 | 1 | 99.0 | 21.5 |

[Note]
(*)2: The amount of pivalic acid is shown by a relative molar amount to a feeding molar amount of 100 of diphenyl carbonate.

EXAMPLE 23

The same reaction and analysis procedures as in Example 1 were carried out with the following exceptions.

Aniline was replaced by 0.012 mole of N-methylaniline, a reaction medium consisting of toluene was added in an amount of 2 ml, and the reaction was carried out at a temperature of 140° C. for 4 hours. In the reaction result, the selectivity of phenyl N-methyl-N-phenylcarbamate was 99.5% and the yield thereof was 91.2%.

The analysis results are shown in Table 6.

reaction result, the selectivity of phenyl N,N-dicyclohexylcarbamate was 70.7% and the yield thereof was 50.4%.

The analysis results are shown in Table 6.

COMPARATIVE EXAMPLE 8

The same reaction and analysis procedures as in Example 25 were carried out except that no pivalic acid was added.

In the reaction result, the selectivity of phenyl N,N-dicyclohexylcarbamate was 32.7% and the yield thereof was 9.5%.

The analysis results are shown in Table 6.

TABLE 6

| Example No. | Monoamine compound | Amount[*]2 of pivalic acid | Reaction temperature (° C.) | Reaction time (hr) | Carbamate selectivity (%) | Carbamate yield (%) |
|---|---|---|---|---|---|---|
| Example |  |  |  |  |  |  |
| 23 | N-methylaniline | 20 | 140 | 4 | 99.5 | 91.2 |
| 24 | Dibenzylamine | 20 | 90 | 6 | 98.5 | 96.1 |
| Comparative Example 7 | Dibenzylamine | 0 | 90 | 6 | 78.5 | 8.3 |
| Example 25 | Dicyclohexylamine | 20 | 150 | 5 | 70.7 | 50.4 |
| Comparative Example 8 | Dicyclohexylamine | 0 | 150 | 5 | 32.7 | 9.5 |

[Note]
[*]2: The amount of pivalic acid is shown by a relative molar amount to a feeding molar amount of 100 of diphenyl carbonate.

EXAMPLE 26

The same reaction and analysis procedures as in Example 1 were carried out with the following exceptions.

Diphenyl carbonate was replaced by 0.01 mole of bis(4-chlorophenyl)carbonate, a reaction medium consisting of nitrobenzene was added in an amount of 5 ml, and the reaction was carried out at a temperature of 60° C. for 8 hours. In the reaction result, the selectivity of 4-chlorophenyl N-phenylcarbamate was 99.3% and the yield thereof was 87.3%.

The analysis results are shown in Table 7.

EXAMPLE 27

The same reaction and analysis procedures as in Example 1 were carried out with the following exceptions.

Diphenyl carbonate was replaced by 0.01 mole of bis(4-nitrophenyl)carbonate, the reaction medium consisting of toluene was added in an amount of 10 ml, and the reaction was carried out at a temperature of 25° C. for 10 hours. In the reaction result, the selectivity of 4-nitrophenyl N-phenylcarbamate was 99.6% and the yield thereof was 98.5%.

The analysis results are shown in Table 7.

EXAMPLE 28

The same reaction and analysis procedures as in Example 1 were carried out with the following exceptions.

Diphenyl carbonate was replaced by 0.01 mole of bis(3,5-dimethoxyphenyl)carbonate, a reaction medium consisting of toluene was added in an amount of 2 ml, and the reaction was carried out at a temperature of 85° C. for 3 hours. In the reaction result, the selectivity of 3,5-dimethoxyphenyl N-phenylcarbamate was 97.4% and the yield thereof was 86.5%.

The analysis results are shown in Table 7.

EXAMPLE 29

The same reaction and analysis procedures as in Example 1 were carried out with the following exceptions.

Diphenyl carbonate was replaced by 0.01 mole of bis(2-tolyl)carbonate, a reaction medium consisting of toluene was added in an amount of 2 ml, and the reaction was carried out at a temperature of 85° C. for 5 hours. In the reaction result, the selectivity of 2-tolyl N-phenylcarbamate was 99.3% and the yield thereof was 71.4%.

The analysis results are shown in Table 7.

TABLE 7

| Example No. | Diaryl carbonate | Reaction temperature (° C.) | Reaction time (hr) | Carbamate selectivity (%) | Carbamate yield (%) |
|---|---|---|---|---|---|
| Example |  |  |  |  |  |
| 26 | (4-ClPhO)$_2$CO | 60 | 8 | 99.3 | 87.3 |
| 27 | (4-NO$_2$PhO)$_2$CO | 25 | 10 | 99.6 | 98.5 |
| 28 | [3,5-(MeO)$_2$PhO]$_2$CO | 85 | 3 | 97.4 | 86.5 |
| 29 | (2-MePhO)$_2$CO | 85 | 15 | 99.3 | 71.4 |

[Note]
(4-ClPhO)$_2$CO: bis(4-chlorophenyl)carbonate
(4-NO$_2$PhO)$_2$CO: bis(4-nitrophenyl)carbonate
[3,5-(MeO)$_2$PhO]$_2$CO: bis(3,5-dimethoxyphenyl)carbonate
(2-MePhO)$_2$CO: bis(2-tolyl)carbonate

EXAMPLES 30 TO 35

In each of Examples 30 to 35, the same reaction and analysis procedures as in Example 1 were carried out with the following exceptions.

A reaction medium consisting of the solvent shown in Table 8 was added in an amount of 4 ml. Also, the reaction time was changed to that shown in Table 8.

The analysis results are shown in Table 8.

TABLE 8

| Example No. | Reaction medium | Reaction temperature (° C.) | Reaction time (hr) | Carbamate selectivity (%) | Carbamate yield (%) |
|---|---|---|---|---|---|
| Example |  |  |  |  |  |
| 30 | Cyclohexane | 75 | 12 | 99.8 | 93.2 |
| 31 | Toluene | 75 | 15 | 99.9 | 93.1 |
| 32 | Chlorobenzene | 75 | 22 | 99.9 | 93.3 |

TABLE 8-continued

| Example No. | Reaction medium | Reaction temperature (° C.) | Reaction time (hr) | Carbamate selectivity (%) | Carbamate yield (%) |
|---|---|---|---|---|---|
| 33 | Anisole | 75 | 23 | 99.7 | 93.2 |
| 34 | Phenol | 75 | 32 | 99.3 | 93.2 |
| 35 | Nitrobenzene | 75 | 22 | 99.9 | 93.4 |

COMPARATIVE EXAMPLES 9 TO 15

In each of Comparative Examples 9 to 15, the same reaction and analysis procedures as in Examples 30 to 35 were carried out except that no pivalic acid was added.

In the reaction result, the yield of phenyl N-phenylcarbamate was 1% or less.

Table 9 shows the melting temperatures and IR spectrums (specific absorption of carbonyl group) of the aryl carbamates obtained in Example 1 and 13 to 29. All the elemental analysis results of these carbamates were consistent with the theoretical values thereof.

TABLE 9

| Example No. | Carbamate | Melting temperature (° C.) | IR spectrum (C = 0) (cm$^{-1}$) |
|---|---|---|---|
| Example | | | |
| 1 | PhNHCO$_2$Ph | 125 | 1716 |
| 13 | 4-ClPhNHCO$_2$Ph | 154 | 1714 |
| 14 | 2-ClPhNHCO$_2$Ph | 56 | 1727, 1759 |
| 15 | 4-MePhNHCO$_2$Ph | 118 | 1719 |
| 16 | 2-MeOPhNHCO$_2$Ph | 47 | 1745 |
| 17 | 4-MeOPhNHCO$_2$Ph | 156 | 1710 |
| 18 | 2-PhPhNHCO$_2$Ph | 89 | 1759 |
| 19 | 2-PhOPhNHCO$_2$Ph | 122 | 1753 |
| 20 | 2-naphthyl-NHCO$_2$Ph | 155 | 1719 |
| 21 | 3-pyridyl-NHCO$_2$Ph | 139 | 1736 |
| 22 | PhCH$_2$NHCO$_2$Ph | 82 | 1702 |
| 23 | Ph(Me)NCO$_2$Ph | 61 | 1719 |
| 24 | (PhCH$_2$)$_2$NCO$_2$Ph | 62 | 1711 |
| 25 | (c-C$_6$H$_{11}$)$_2$NCO$_2$Ph | 82 | 1704 |
| 26 | PhNHCO$_2$-(4-ClPh) | 91 | 1718 |
| 27 | PhNHCO$_2$-(4-NO$_2$Ph) | 157 | 1754 |
| 28 | PhNHCO$_2$-(3,5-(MeO)$_2$Ph) | 91 | 1711 |
| 29 | PhNHCO$_2$-(2-MePh) | 149 | 1713 |

[Note]
4-ClPh: 4-chlorophenyl group,
2-ClPh: 2-chlorophenyl group,
4-MePh: 4-methylphenyl group,
2-MeOPh: 2-methoxyphenyl group,
4-MeOPh: 4-methoxyphenyl group,
2-PhPh: 2-biphenyl group,
2-PhOPh: 2-phenoxyphenyl group,
2-naphthyl: 2-naphthyl group,
3-pyridyl: 3-pyridyl group
c-C$_6$H$_{11}$: cyclohexyl group,
4-NO$_2$Ph: 4-nitrophenyl group,
3,5-MeOPh: 3,5-dimethoxyphenyl group,
2-MePh: 2-methylphenyl group

EXAMPLE 36

A glass reactor having an inside volume of 5 ml was charged with a mixture of 0.01 mole (3.2 mole/liter) of diphenyl carbonate, 0.012 mole (3.8 mole/liter) of aniline and 0.002 mole (0.6 mole/liter) of acetic acid. The mixture was heated and stirred at a bath temperature of 85° C. under the ambient atmospheric pressure for 5 hours.

After the reaction was completed, the reaction mixture liquid was analyzed by high performance liquid chromatography. It was confirmed that the selectivity of phenyl N-phenyl carbamate was 99.3%, and the yield thereof was 94.9%. Also, it was confirmed that during the reaction for 5 hours, phenyl N-phenylcarbamate was produced in an amount of 9.49 millimoles.

EXAMPLES 37 TO 39

In each of Examples 37 to 39, the same reaction and analysis procedures as in Example 36 were carried out with the following exceptions.

Acetic acid was replaced by 0.002 mole (0.6 mole/liter) of the carboxylic acid shown in Table 10, and the reaction was carried out at the temperature for the time as shown in Table 10. The analysis results are shown in Table 10.

TABLE 10

| Example No. | Diaryl carbonate | Reaction temperature (° C.) | Reaction time (hr) | Carbamate selectivity (%) | Carbamate yield (%) |
|---|---|---|---|---|---|
| Example | | | | | |
| 36 | Acetic acid | 85 | 5 | 99.3 | 94.9 |
| 37 | Propionic acid | 75 | 4 | 99.8 | 97.2 |
| 38 | Isovaleric acid | 75 | 4 | 99.8 | 89.0 |
| 39 | Chloroacetic acid | 75 | 4 | 99.7 | 89.6 |

COMPARATIVE EXAMPLE 9

The same reaction and analysis procedures as in Example 36 were carried out with the following exceptions.

The feeding amount of acetic acid was changed to 0.000013 mole (0.004 mole/liter), and toluene was added in an amount of 0.12 ml.

In the reaction result, the selectivity of phenyl N-phenylcarbamate was 98.5% and the yield thereof was 64.5%. Also, it was confirmed that during the reaction for 5 hours, only 6.4 millimoles of phenyl N-phenylcarbamate could be produced.

The analysis results of Example 36 and Comparative Example 9 are shown in Table 11.

TABLE 11

| Example No. | Concentration of acetic acid (mole/liter) | Carbamate selectivity (%) | Carbamate yield (%) | Carbamate yield (millimole) |
|---|---|---|---|---|
| Example 36 | 0.6 | 99.3 | 94.9 | 9.49 |
| Comparative Example 9 | 0.004 | 98.5 | 64.5 | 6.45 |

EXAMPLE 40

A glass reactor having an inside volume of 5 ml was charged with a mixture of 0.01 mole (2.4 mole/liter) of diphenyl carbonate, 0.012 mole (2.9 mole/liter) of aniline and 0.002 mole (0.48 mole/liter) of acetic acid. The mixture was heated and stirred at a bath temperature of 80° C. under the ambient atmospheric pressure for 7 minutes.

After the reaction was completed, the reaction mixture liquid was analyzed in the same manner as in Example 36. It was confirmed that the selectivity of phenyl N-phenyl carbamate was 99.9%, and the yield thereof was 20.1%. Also, it was confirmed that, in the 7 minute reaction, 2.01 millimoles of phenyl N-phenylcarbamate were produced at a synthesis rate of 0.288 millimole/minute.

COMPARATIVE EXAMPLE 10

The same reaction and analysis procedures as in Example 40 were carried out with the following exceptions.

The feeding amount of diphenyl carbonate was changed to 0.0013 mole (0.3 mole/liter), and toluene was added in an amount of 2.67 ml. In the reaction result, the selectivity of phenyl N-phenylcarbamate was 99.9% and the yield thereof was 27.0%. In the above-mentioned 7 minute reaction, phenyl N-phenylcarbamate was produced only in an amount of 0.35 millimole at a synthesis rate of 0.049 millimole/minute.

COMPARATIVE EXAMPLE 11

The same reaction and analysis procedures as in Example 40 were carried out with the following exceptions.

The feeding amount of aniline was changed to 0.0013 mole (0.31 mole/liter), and toluene was added in an amount of 2.0 ml.

In the reaction result, the selectivity of phenyl N-phenylcarbamate was 99.9% and the yield thereof was 20.5%. It was confirmed that, in the 7 minute reaction, phenyl N-phenylcarbamate was produced only in an amount of 0.27 millimoles, a synthesis rate of 0.038 millimole/minute. The selectivity and yield are based on the amount of aniline.

The analysis results of Example 40 and Comparative Examples 10 and 11 are shown in Table 12.

tate the resultant white crystals of phenyl N-phenylcarbamate. The crystals were isolated by filtration from the reaction mixture liquid, the isolated crystals were washed twice with cyclohexane, and dried under reduced pressure. Phenyl N-phenylcarbamate was obtained in an amount of 1.59 g. Further, the filtrate from the above-mentioned filtration was concentrated, the precipitated crystals from the filtrate were isolated by filtration and treated in the same manner as mentioned above. Phenyl N-phenylcarbamate was obtained in an amount of 0.25 g. The total yield of phenyl N-phenylcarbamate was 86.3%. The resultant phenyl N-phenylcarbamate had a degree of purity of 98% by weight or more, and the content of N,N'-diphenylurea contained therein was 0.3% by weight or less.

EXAMPLE 42

The same reaction and analysis procedures as in Example 41 were carried out with the following exceptions.

Pivalic acid was replaced by 0.002 mole of benzoic acid. The total yield of phenyl N-phenylcarbamate was 83.5%, and the degree of purity thereof was 98% by weight or more. Also, the content of N,N'-diphenylurea was 0.8% by weight.

EXAMPLE 43

A glass reactor having an inside volume of 200 ml was charged with a mixture of 0.2 mole of diphenyl carbonate, 0.24 mole of aniline and 0.04 mole of acetic acid. The mixture was heated and stirred at a bath temperature of 75° C. under the ambient atmospheric pressure for 3.5 hours.

After the reaction was completed, the reaction mixture was dissolved in 200 ml of ethyl acetate, the solution was washed with an aqueous hydrochloric acid solution (prepared from 5.5g of a 36 weight % hydrochloric acid and 50 ml of water) and then dried on anhydrous magnesium sulfate. Then, from the resultant organic phase, ethyl acetate and phenol were removed by distillation, and the resultant crude carbamate in an amount of 49.13 g was subjected to recrystallization with 80 ml of toluene. The refined phenyl N-phenylcarbamate was obtained in an amount of 35.18 g.

TABLE 12

| Example No. | Concentration of diphenyl carbonate (mole/liter) | Concentration of aniline (mole/liter) | Selectivity of carbamate (%) | Yield of carbamate (%) | Yield of carbamate (millimole) | Synthesis rate of carbamate (millimole/minute) |
| --- | --- | --- | --- | --- | --- | --- |
| Example 40 | 2.4 | 2.9 | 99.9 | 20.1 | 2.01 | 0.288 |
| Comparative Example | | | | | | |
| 10 | 0.3 | 2.9 | 99.9 | 27.0 | 0.35 | 0.049 |
| 11 | 2.7 | 0.31 | 99.9 | 20.5 | 0.27 | 0.038 |

EXAMPLE 41

A glass reaction vessel equipped with a reflux condenser and having an inside volume of 20 ml was charged with a mixture of 0.01 mole of diphenyl carbonate, 0.012 mole of aniline, 0.002 mole of pivalic acid and 4 ml of cyclohexane. The mixture was heated and stirred at a bath temperature of 85° C. under the ambient atmospheric pressure for 5 hours.

After the reaction was completed, the reaction mixture liquid was cooled to room temperature (25° C.), to precipi- Further, the recrystallization mother liquid was concentrated, the resultant precipitated solid substance was recrystallized from toluene, to obtain 2.16 g of phenyl N-phenylcarbamate. The total yield of phenyl N-phenylcarbamate collected by the above-mentioned procedures was 87.6%. Also, the resultant phenyl N-phenylcarbamate had a degree of purity of 99.5% by weight and a content of N,N'-diphenylurea of 0.1% by weight.

EXAMPLE 44

A glass reactor having an inside volume of 5 ml was charged with a mixture of 6 mmole of diphenyl carbonate, 2 mmole of 4,4'-diaminodiphenylmethane, 0.4 mmole of pivalic acid and 1 ml of phenol. The mixture was heat-reacted at a temperature of 90° C. under the ambient atmospheric pressure for 6 hours.

After the reaction was completed, the reaction mixture liquid was analyzed by high performance liquid chromatography. It was confirmed that diphenyl (methylene-di-1,4-phenylene) biscarbamate was produced at a yield of 86.3% and phenyl N-[4-(4'-aminobenzyl)phenyl] carbamate was produced at a yield of 11.7%.

COMPARATIVE EXAMPLE 12

The same reaction and analysis procedures as in Example 44 were carried out except that no pivalic acid was added.

In the reaction result, diphenyl (methylene-1,4-phenylene)biscarbamate was produced at a yield of 4.7% and phenyl N-[4-(4'-aminobenzyl)phenyl] carbamate was produced at a yield of 27.9%.

EXAMPLE 45

The same reaction and analysis procedures as in Example 44 were carried out with the following exceptions. 4,4'-diaminodiphenylmethane was replaced by 2 mmole of o-tolidine, the reaction time was changed to 8 hours and no phenol was added to the reaction mixture. In the reaction result, diphenyl [3,3'-dimethyl(1,1'-biphenyl-4,4'-diyl] biscarbamate was produced at a yield of 78.7%, and phenyl N-[4-(4'-amino-3'-methylphenyl)-2-methylphenyl] carbamate was produced at a yield of 20.8%.

COMPARATIVE EXAMPLE 13

The same reaction and analysis procedures as in Example 45 were carried out, except that no pivalic acid was added.

In the reaction result, diphenyl [3,3'-dimethyl(1,1'-biphenyl)-4,4'-diyl]biscarbamate was produced at a yield of 0.4%, and phenyl N-[4(4'-amino-3'-methyl)phenyl]2-toluylcarbamate was produced at a yield of 0.7%.

EXAMPLE 46

The same reaction and analysis procedures as in Example 44 were carried out with the following exceptions.

4,4'-diaminodiphenylmethane was replaced by 2 mmole of 2,4-diaminotoluene, phenol was replaced by 1 ml of toluene, and the reaction time was changed to 16 hours. In the reaction result, diphenyl (4-methyl-1,3-phenylene) biscarbamate was produced at a yield of 71.3%, and phenyl N-(3-amino-4-methylphenyl)carbamate was produced at a yield of 21.3%.

COMPARATIVE EXAMPLE 14

The same reaction and analysis procedures as in Example 46 were carried out except that no pivalic acid was added.

In the reaction result, diphenyl (4-methyl-1,3-phenylene) biscarbamate was produced at a yield of 0.4%, and phenyl N-(3-amino-4-methylphenyl)carbamate was produced at a yield of 20.7%.

EXAMPLE 47

The same reaction and analysis procedures as in Example 44 were carried out with the following exceptions.

The 5 ml glass reactor was replaced by a glass reactor having a capacity of 20 ml, 4,4'-diaminodiphenylmethane was replaced by 2 mmole of m-xylylenediamine, phenol was replaced by 10 ml of methylene chloride, the reaction temperature was changed to 25° C., and the reaction time was changed to 1.5 hours. In the reaction result, diphenyl [1,3-phenylene(bismethylene)]biscarbamate was produced at a yield of 90.8%.

COMPARATIVE EXAMPLE 15

The same reaction and analysis procedures as in Example 47 were carried out except that no pivalic acid was added. In the reaction result, diphenyl [1,3-phenylene(bismethylene)]biscarbamate was obtained at a yield of 65.4%.

EXAMPLE 48

The same reaction and analysis procedures as in Example 44 were carried out with the following exceptions.

4,4'-diaminodiphenylmethane was replaced by 2 mmoles of p-phenylenediamine, phenol was replaced by 1 ml of chlorobenzene, and the reaction time was changed to 7 hours. In the reaction result, diphenyl 1,4-phenylenebiscarbamate was produced at a yield of 89.7%, and phenyl N-(4-aminophenyl)carbamate was produced at a yield of 7.4%.

COMPARATIVE EXAMPLE 16

The same reaction and analysis procedures as in Example 48 were carried out except that no pivalic acid was added. In the reaction result, the yield of diphenyl 1,4-phenylenebiscarbamate was 4.4%, and the yield of phenyl N-(4-aminophenyl)carbamate was 60.0%.

EXAMPLE 49

The same reaction and analysis procedures as in Example 44 were carried out with the following exceptions.

4,4'-diaminodiphenylmethane was replaced by 2 mmoles of 4,4'-diaminodiphenylether, phenol was replaced by 1 ml of toluene, and the reaction time was changed to 9 hours. In the reaction result, diphenyl (oxydi-1,4-phenylene) bicarbamate was produced at a yield of 97.3%, and phenyl N-[4-(4'-aminophenoxy)phenyl] carbamate was produced at a yield of 2.1%.

COMPARATIVE EXAMPLE 17

The same reaction and analysis procedures as in Example 49 were carried out except that no pivalic acid was added. In the reaction result, the yield of diphenyl (oxydi-1,4-phenylene) biscarbamate was 0.1%, and the yield of phenyl N-[4-(4'-aminophenoxy)phenyl] carbamate was 1.9%.

EXAMPLE 50

The same reaction and analysis procedures as in Example 44 were carried out with the following exceptions.

The 5 ml glass reactor was replaced by a glass reactor having a capacity of 20 ml, 4,4'-diaminodiphenylmethane was replaced by 2 mmole of anhydrous piperazine, phenol was replaced by 10 ml of methylene chloride, the reaction temperature was changed to 25° C., and the reaction time was changed to 3 hours. In the reaction result, N,N'-piperazinebisphenyl carboxylate was produced at a yield of 96.4%.

COMPARATIVE EXAMPLE 18

The same reaction and analysis procedures as in Example 50 were carried out except that no pivalic acid was added.

In the reaction result, the yield of N,N'-piperazinebisphenyl carboxylate was 84.3%.

The compositions of the reaction mixture, the reaction conditions, and analysis results of Examples 44 to 50 and Comparative Examples 12 to 18 are shown in Table 13.

tion. The solid substance was dried under reduced pressure, and was analysed by high performance liquid chromatography. In the analysis result, diphenyl [3,3'-dimethyl(1,1-biphenyl)-4,4'-diyl] biscarbamate having a degree of purity of 99% or more was obtained at a yield of 91.1%.

TABLE 13

| | | | Item | | | | |
|---|---|---|---|---|---|---|---|
| Example No. | Amine compound | Pivalic acid (mmol) | Reaction medium | Reaction temperature (° C.) | Reaction time (hr) | Yield of biscarbamate (%) | Yield of monocarbamate (%) |
| Example 44 | 4,4'-diaminodiphenylmethane | 0.4 | Phenol | 90 | 6 | 86.3 | 11.7 |
| Comparative Example 12 | 4,4'-diaminodiphenylmethane | — | Phenol | 90 | 6 | 4.7 | 27.9 |
| Example 45 | o-tolidine | 0.4 | — | 90 | 8 | 78.7 | 20.8 |
| Comparative Example 13 | o-tolidine | — | — | 90 | 8 | 0.4 | 0.7 |
| Example 46 | 2,4-diaminotoluene | 0.4 | Toluene | 90 | 16 | 71.3 | 21.3 |
| Comparative Example 14 | 2,4-diaminotoluene | — | Toluene | 90 | 16 | 0.4 | 20.7 |
| Example 47 | m-xylylenediamine | 0.4 | Methylene chloride | 25 | 1.5 | 90.8 | — |
| Comparative Example 15 | m-xylylenediamine | — | Methylene chloride | 25 | 1.5 | 65.4 | — |
| Example 48 | p-phenylenediamine | 0.4 | Chlorobenzene | 90 | 7 | 89.7 | 7.4 |
| Comparative Example 16 | p-phenylenediamine | — | Chlorobenzene | 90 | 7 | 4.4 | 60.0 |
| Example 49 | 4,4'-diaminodiphenylether | 0.4 | Toluene | 90 | 9 | 97.3 | 2.1 |
| Comparative Example 17 | 4,4'-diaminodiphenylether | — | Toluene | 90 | 9 | 0.1 | 1.9 |
| Example 50 | Anhydrous piperazine | 0.4 | Methylene chloride | 25 | 3 | 96.4 | — |
| Comparative Example 18 | Anhydrous piperazine | — | Methylene chloride | 25 | 3 | 84.3 | — |

EXAMPLE 51

A glass reactor having a capacity of 20 ml was charged with a mixture of 24 mmole of diphenyl carbonate, 4 mmole of 4,4'-diaminodiphenylmethane, 0.8 mmole of pivalic acid and 2 ml of chlorobenzene. The mixture was stirred at a temperature of 90° C. under the ambient atmospheric pressure for 6 hours.

After the reaction was completed, the reaction mixture liquid was cooled to room temperature, the precipitated solid substance was isolated by filtration, the filtration residue was added with 3 ml of chlorobenzene, and the precipitated solid substance was isolated by filtration. The resultant solid substance was dried under reduced pressure and then was analysed by high performance liquid chromatography. In the analysis result, diphenyl (methylene-di-1,4-phenylene) bis-carbamate having a degree of purity of 99% or more was obtained at a yield of 91.2%.

EXAMPLE 52

The same reaction as in Example 51 was carried out with the following exceptions.

4,4'-diaminodiphenylmethane was replaced by 4 mmole of o-tolidine, chlorobenzene was replaced by 2 ml of toluene, and the reaction time was changed to 24 hours.

After the reaction was completed, the resultant reaction mixture liquid was cooled to room temperature, the precipitated solid substance was separated by filtration, the filtration residue was added with 3 ml of toluene, and the resultant precipitated solid substance was isolated by filtra-

EXAMPLE 53

The same reaction and isolation of reaction product as in Example 1 were carried out with the following exceptions.

4,4'-diaminodiphenylmethane was replaced by 4 mmoles of 1,5-naphthalenediamine, chlorobenzene was employed in an amount of 4 ml, the reaction temperature was changed to 130° C. and the reaction time was changed to 13 hours. In the reaction result, diphenyl 1,5-naphthalene biscarbamate was obtained at a yield of 71.5%.

EXAMPLE 54

A glass reactor having an inside volume of 50 ml was charged with a mixture of 24 mmoles of diphenyl carbonate, 4 mmoles of m-xylylenediamine, 0.8 mmole of pivalic acid and 10 ml of methylene chloride. The mixture was stirred at a temperature of 25° C. under the ambient atmospheric pressure for 7 hours.

After the reaction was completed, the solid substance precipitate from the reaction mixture liquid was isolated by filtration, washed with methylene chloride, and recrystallized from acetonitrile. The resultant solid substance was dried under reduced pressure, and analysed by high performance liquid chromatography. In the analysis result, diphenyl (1,3-phenylene (bismethylene) biscarbamate having a degree of purity of 98% or more was obtained at a yield of 73.1%.

The results of Examples 51 to 54 are shown in Table 14.

TABLE 14

| Example No. | Amine compound | Reaction medium | Reaction temperature (° C.) | Reaction time (hr) | Yield of carbamate (%) |
|---|---|---|---|---|---|
| Example | | | | | |
| 51 | 4,4'-diaminodiphenyl-methane | Chlorobenzene | 90 | 6 | 91.2 |
| 52 | o-tolidine | Toluene | 90 | 24 | 91.1 |
| 53 | 1,5-naphthalene-diamine | Chlorobenzene | 130 | 13 | 71.5 |
| 54 | m-xylylenediamine | Methylene chloride | 25 | 7 | 73.1 |

EXAMPLES 55 TO 59

In each of Examples 55 to 59, the same reaction and analysis procedures as in Example 44 were carried out with the following exceptions.

Phenol was replaced by 1 ml of the solvent shown in Table 15, and the reaction time was changed to that shown in Table 15.

The analysis results are shown in Table 15.

TABLE 15

| Example No. | Reaction medium | Reaction temperature (° C.) | Reaction time (hr) | Yield of biscarbamate (%) | Yield of mono-carbamate (%) |
|---|---|---|---|---|---|
| Example | | | | | |
| 55 | Propionitrile | 90 | 6 | 89.6 | 8.3 |
| 56 | Chlorobenzene | 90 | 6 | 94.8 | 4.5 |
| 57 | Toluene | 90 | 6 | 95.0 | 3.0 |
| 58 | Nitrobenzene | 90 | 6 | 95.9 | 3.4 |
| 59 | Cyclohexane | 90 | 6 | 96.8 | 2.5 |

EXAMPLE 60

A glass reactor having an inside volume of 5 ml was charged with a mixture of 12 mmoles of diphenyl carbonate, 2 mmoles of m-phenylenediamine and 0.4 mmole of acetic acid. The mixture was subjected to a reaction at a temperature of 90° C. under the ambient atmospheric pressure for 6 hours.

After the reaction was completed, the reaction mixture liquid was analyzed by high performance liquid chromatography. It was confirmed that diphenyl 1,3-phenylenebiscarbamate was produced at a yield of 88.8%, and phenyl N-(3-aminophenyl) carbamate was produced at a yield of 10.6%.

EXAMPLES 61 TO 63

In each of Examples 61 to 63, the same reaction and analysis procedures as in Example 60 were carried out except that acetic acid was replaced by 0.4 mmole of the carboxylic acid shown in Table 16.

The analysis results are shown in Table 16.

COMPARATIVE EXAMPLE 19

The same reaction and analysis procedures as in Example 60 were carried out except that no acetic acid was added. In the reaction result, the yield of diphenyl 1,3-phenylenebiscarbamate was 2.1%, and the yield of phenyl N-(3-amino-phenyl) carbamate was 5.9%.

The results of Examples 60 to 63 and Comparative Example 19 are shown in Table 10.

TABLE 10

| Example No. | Protonic acid | Yield of biscarbamate (%) | Yield of monocarbamate (%) |
|---|---|---|---|
| Example | | | |
| 60 | Acetic acid | 88.8 | 10.6 |
| 61 | Propionic acid | 90.2 | 8.7 |
| 62 | Pivalic acid | 92.4 | 7.1 |
| 63 | Benzoic acid | 94.9 | 4.8 |
| 19 | — | 2.1 | 5.9 |

EXAMPLE 64

A glass reactor having an inside volume of 50 ml was charged with a mixture of 60 mmoles of diphenyl carbonate, 10 mmoles of 4,4'-diaminodiphenylmethane, 2 mmoles of benzoic acid and 12.75 ml of chlorobenzene. The mixture was stirred at a temperature of 80° C. under the ambient atmospheric pressure for 16 hours.

After the reaction was completed, the reaction mixture liquid was analyzed by high performance liquid chromatography. It was confirmed that diphenyl (methylenedi-1,4-phenylene) biscarbamate was produced in an amount of 9.7 mmoles and phenyl N-[4-(4'-aminobenzyl)phenyl] carbamate was produced in an amount of 0.2 mmole.

Then, the resultant reaction mixture liquid was cooled to room temperature, the precipitated solid substance is separated by filtration, the remaining filtrate was added with 3 ml of chlorobenzene, and the precipitated solid substance was collected by filtration. The resultant solid substance was dried under reduced pressure and subjected to high performance liquid chromatographic analysis. It was confirmed that diphenyl (methylenedi-1,4-phenylene) biscarbamate having a degree of purity of 99% or more was obtained in an amount of 9.3 mmoles.

EXAMPLE 65

The same filtrate as that obtained by filtering the reaction mixture liquid of Example 64 to collect the precipitated solid substance, was washed with 100 ml of a 5 weight % aqueous NaOH solution, to separate and remove benzoic acid and phenol. To the separation residual liquid was added 18.6 mmoles of diphenyl carbonate, 9.3 mmoles of 4,4'-diaminodiphenylmethane and 2 mmoles of benzoic acid. The resultant mixture liquid was concentrated to such an extent that the content of chlorobenzene in the mixture liquid became equal to the content of 12.75 ml in Example 64, and the concentrated liquid was subjected to the same reaction and analysis procedures as in Example 64.

As a result, it was confirmed that 9.5 mmoles of diphenyl (methylenedi-1,4-phenylene) biscarbamate and 0.3 mmole of phenyl N-[4-(4'-aminobenzyl)phenyl] carbamate were produced.

Successively, the reaction mixture liquid was subjected to the same treatment as in Example 64. As a result, 9.0 mmoles of diphenyl (methylenedi-1,4-phenylene) biscarbamate having a degree of purity of 99% or more were obtained.

EXAMPLE 66

The same filtrate as that obtained by filtering the reaction mixture liquid of Example 65 to collect the precipitated solid substance, was washed with 100 ml of a 5 weight % aqueous NaOH solution, to separate and remove benzoic acid and phenol. To the separation residual liquid was added 17.9 mmoles of diphenyl carbonate, 9.0 mmoles of 4,4'-diaminodiphenylmethane and 2 mmoles of benzoic acid. The resultant mixture liquid was concentrated to such an extent that the content of chlorobenzene in the mixture liquid became equal to the content of 12.75 ml in Example 64, and the concentrated liquid was subjected to the same reaction and analysis procedures as in Example 64.

As a result, it was confirmed that 9.5 mmoles of diphenyl (methylenedi-1,4-phenylene) biscarbamate and 0.2 mmole of phenyl N-[4-(4'-aminobenzyl)phenyl] carbamate were produced.

Successively, the reaction mixture liquid was subjected to the same treatment as in Example 64. As a result, 8.8 mmoles of diphenyl (methylenedi-1,4-phenylene) biscarbamate having a degree of purity of 99% or more were obtained.

EXAMPLE 67

A glass reactor having an inside volume of 500 ml was charged with a mixture of 0.9 mole of diphenyl carbonate, 0.15 mole of 4,4'-diaminodiphenylmethane, 30 mmoles of pivalic acid and 150 ml of toluene. The mixture was stirred at a temperature of 80° C. under the ambient atmospheric pressure for 16 hours.

After the reaction was completed, the reaction mixture liquid was analyzed by high performance liquid chromatography. It was confirmed that 0.143 mole of diphenyl (methylenedi-1,4-phenylene) biscarbamate and 0.003 mole of phenyl N-[4-(4'-aminobenzyl)phenyl] carbamate were produced.

Then, the resultant reaction mixture liquid was cooled to room temperature, the precipitated solid substance was separated by filtration, the remaining filtrate was added with 50 ml of toluene, and the precipitated solid substance was collected by filtration. The resultant solid substance was dried under reduced pressure and subjected to high performance liquid chromatographic analysis. It was confirmed that diphenyl (methylenedi-1,4-phenylene) biscarbamate having a degree of purity of 99% or more was obtained in an amount of 0.141 mole.

EXAMPLE 68

The same filtrate as that obtained by filtering the reaction mixture liquid of Example 67 to collect the precipitated solid substance, was concentrated under reduced pressure to remove toluene, phenol and pivalic acid. To the concentrated liquid was added 0.302 mole of diphenyl carbonate, 0.141 mole of 4,4'-diaminodiphenylmethane 30 mmoles of pivalic acid and 150 ml of toluene. The resultant mixture liquid was subjected to the same reaction and analysis procedures as in Example 27.

As a result, it was confirmed that 0.140 mole of diphenyl (methylenedi-1,4-phenylene) biscarbamate and 0.003 mole of phenyl N-[4-(4'-aminobenzyl)phenyl] carbamate were produced.

Then, the solid substance precipitated in the reaction mixture liquid obtained by the above-mentioned reaction was collected by filtration, and the resultant filtrate was subjected to the same procedures as in Example 67. As a result, 0.138 mole of diphenyl (methylenedi-1,4-phenylene) biscarbamate having a degree of purity of 99% or more was obtained.

As the above-mentioned examples clearly illustrate, the process of the present invention for producing an aryl carbamate can produce the aryl carbamate under moderate conditions without using materials having a stimulative property and/or a toxicity, without employing a base, without producing by-products such as urea derivatives or acid amides, and without necessitating an expensive catalyst, in a high yield, with a high degree of purity and at a high selectivity.

Also, in the process of the present invention, the resultant aryl carbamate can be easily isolated and collected from the reaction mixture liquid and refined.

What is claimed is:

1. A process for producing an aryl carbamate comprising reacting a diaryl carbonate with an amine compound having at least one hydrogen atom located at an N-position in the presence of at least one carboxylic acid of the formula (I):

$$R^1\text{—COOH} \quad (I)$$

in which $R^1$ is a member selected from the group consisting of (1) $C_3$–$C_{15}$ alkyl groups having an α-positioned carbon atom bonded to the —COOH group and to only one hydrogen atom and $C_5$–$C_{15}$ cycloalkyl groups having an α-positioned carbon atom bonded to the —COOH group and to only one hydrogen atom, (2) $C_4$–$C_{16}$ alkyl groups which may include a cycloalkyl structure, having an α-positioned carbon atom bonded to the —COOH group and to no hydrogen atom, (3) $C_6$–$C_{16}$ aryl groups, and (4) $C_4$–$C_{15}$ heterocyclic groups.

2. The process of claim 1, wherein the carboxylic acid reacted with the diaryl carbonate is ina concentration of 0.5 mole/liter or more.

3. The process of claim 1, wherein the amine compound is selected from the group consisting of compounds represented by the formulae (III), (IV), (V), (VI), and (VII);

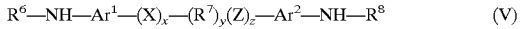

$$R^3\text{—NH}_2 \quad (III)$$

$$R^4\text{—NH—}R^5 \quad (IV)$$

$$R^6\text{—NH—Ar}^1\text{—(X)}_x\text{—(R}^7)_y\text{(Z)}_z\text{—Ar}^2\text{—NH—}R^8 \quad (V)$$

$$R^9\text{—NH—}R^{10}\text{—NH—}R^{11} \quad (VI)$$

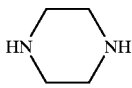

(VII)

in which $R^3$ is a member selected from the group consisting of an aralkyl group, an aryl group, a pyrrolyl group, an indolyl group, a pyridyl group, a quinolyl group, an isoquinolyl group, an acridinyl group, a triazinyl group, an imidazolyl group, a pyrazolyl group, a triazolyl group, a tetrazolyl group, a pyrimidyl group, a thiazolyl group, an isothiazolyl group, a benzothiazolyl group, a thiadiazolyl group, a furanyl group, a benzofuranyl group, a cumarinyl group, an isoxazolyl group and a benzoxazolyl group;

$R^4$ and $R^5$ respectively and independently from each other represent a member selected from the group consisting of alkyl groups, aralkyl groups, aryl groups and nitrogen-containing heterocyclic groups, wherein $R^4$ and $R^5$ may be bonded with each other to form a fused cyclic structure, and wherein each of said alkyl, aralkyl, aryl, and heterocyclic groups may have one or more substituents selected from the group consisting of alkyl groups, aryl groups, alkoxy groups, aryloxy groups, halogen atoms, a nitro group and a cyano group;

$R^6$ and $R^8$ respectively and independently from each other represent a member selected from the group consisting of alkyl groups and aralkyl groups, each of which groups may have one or more substituents selected from the group consisting of alkyl groups, alkoxy groups, aryl groups, acyl groups, aryloxy groups, halogen atoms, a nitro group and a cyano group;

$Ar^1$ and $Ar^2$ respectively and independently from each other represent a member selected from arylene groups each of which may have one or more substituents selected from the group consisting of alkyl groups, alkoxy groups, aryl groups, acyl groups, aryloxy groups, halogen atoms, a nitro group and a cyano group;

$R^7$ represents a member selected from the group consisting of alkylene groups, alkenylene groups, aralkylene groups and arylene groups, each of which groups may have one or more substituents selected from the group consisting of alkyl groups, alkoxy groups, aryl groups, acyl groups, aryloxy groups, halogen atoms, a nitro group and a cyano group;

X and Z respectively and independently from each other represent a divalent group selected from the group consisting of alkylene groups, and —NH—, —O—, —S—, —SS—, —SO$_2$— and —CO— groups;

z, x, y and z respectively and independently from each other represent an integer of 0 to 1;

$R^9$ and $R^{11}$ respectively and independently from each other represent a member selected from the group consisting of a hydrogen atom, alkyl groups, aralkyl groups and aryl groups, wherein each of the alkyl, aralkyl and aryl groups may have one or more substituents selected from the group consisting of alkyl groups, alkoxy groups, aryl groups, acyl groups, aryloxy groups, halogen atoms, a nitro group and a cyano group;

$R^{10}$ represents a member selected from the group consisting of alkylene groups, aralkylene groups, and arylene groups, each of which groups may have one or more substituents selected from the group consisting of alkyl groups, alkoxy groups, aryl groups, acyl groups, aryloxy groups, halogen atoms, a nitro group and a cyano group; and the compound of formula (VII) may have one or more substituents selected from the group consisting of alkyl groups, alkoxy groups, aryl groups, acyl groups, aryloxy groups, halogen atoms, a nitro group and a cyano group.

4. The process of claim 3, wherein the amine compound is selected from the group consisting of aromatic primary amines of the formula (III) wherein $R^3$ is an aryl group and aromatic secondary amines and aliphatic secondary amines of the formula (IV) wherein $R^4$ and $R^5$ respectively and independently from each other represent an alkyl group or an aryl group.

5. The process of claim 1, wherein the carboxylic acids of the formula (I) are selected from the group consisting of aliphatic carboxylic acids in which $R^1$ is a $C_4$–$C_{16}$ alkyl group of which the α-positioned carbon atom is not bonded to a hydrogen atom; cycloaliphatic carboxylic acids in which $R^1$ is a $C_5$–$C_{15}$ cycloalkyl group of which the α-positioned carbon atom is not bonded to a hydrogen atom; aromatic carboxylic acids in which $R^1$ is a $C_6$–$C_{16}$ aryl group; and heterocyclic carboxylic acids in which $R^1$ is a $C_4$–$C_{15}$ heterocyclic group.

6. The process of claim 3, wherein the carboxylic acid reacted with the diaryl carbonate is fed in a molar amount of 0.005 to 5 times the molar amount of the diaryl carbonate fed into the reaction, and at least one member selected from the group consisting of the amine compounds of formulae (III) and (IV) is fed into the reaction in a molar amount of 0.05 to 20 times the molar amount of the diaryl carbonate.

7. The process of claim 6, wherein the reaction is carried out at a temperature in the range of from −30° C. to 200° C.

8. The process of claim 6, wherein the reaction is carried out in a reaction medium in an amount of 50 parts by weight or less per parts by weight of the diaryl carbonate fed into the reaction.

9. The process of claim 3, wherein at least one amine compound selected from the group consisting of the amine compounds of formulae (V) to (VII) is present and the carboxylic acid is present in a molar amount of 0.001 to 5 times the molar amount of said at least one amine compound.

10. The process of claim 9, wherein the amine compound is present in a molar amount of 0.01 to 0.5 times the molar amount of the diaryl carbonate.

11. The process of claim 9, wherein the reaction is carried out at a temperature of from 0° C. to 200° C.

12. The process of claim 9, wherein the reaction is carried out in a reaction medium, which is non-reactive or substantially non-reactive reactive to the diaryl carbonate, the at least one amine compound, the carboxylic acid and the aryl carbamate produced, in a weight amount of 50 times or less the weight amount of the at least one amine compound.

13. The process of claim 8 or 12, wherein the reaction medium comprises at least one member selected from the group consisting of aliphatic alcohols, aliphatic hydrocarbons, aromatic hydrocarbons, ethers, nitrites, aliphatic halogenated hydrocarbons, amide compounds, phenol compounds, and nitro compounds.

14. The process of claim 1, further comprising, after the reaction is completed, precipitating the aryl carbamate from a resultant reaction product-containing mixture at a temperature of 40° C. or less, and isolating and collecting the precipitated aryl carbamate from the mixture.

15. The process of claim 14, wherein the precipitation of the aryl carbamate is carried out at a temperature of from −30 to 40° C.

16. The process of claim 14, wherein after the reaction is completed, a non-reacted portion of the amine compound is removed from the reaction product containing mixture, and then the aryl carbamate is isolated and collected from the non-reacted amine compound-removed mixture.

17. The process of claim 5, wherein the aliphatic carboxylic acids are selected from the group consisting of isobutylic acid, 2-methylbutylic acid, pivalic acid, triethylacetic acid and 2,2,-dimethylbutylic acid; the cycloaliphatic carboxylic acids are selected from the group consisting of cyclopentane carboxylic acid, cyclohexane carboxylic acid, 1-methylcyclohexane carboxylic acid, decaline carboxylic acid and 1-adamantine carboxylic acid; the aromatic carboxylic acids are selected from benzoic acid, fluorobenzoic acid, chlorobenzoic acid, dichlorobenzoic acid, toluic acid, anisic acid, salicylic acid, naphthalene carboxylic acid, anthracene carboxylic acid, phthalic acid, isopthalic acid and terephthalic acid; and the heterocyclic carboxylic acids are selected from the group consisting of furan carboxylic acid, thiophene carboxylic acid, pyridine carboxylic acid and pyrrole carboxylic acid.

* * * * *

UNITED STATES PATENT AND TRADEMARK OFFICE
CERTIFICATE OF CORRECTION

PATENT NO.   : 6,143,917
DATED        : November 7, 2000
INVENTOR(S)  : Katsumasa Harada et al.

Page 1 of 1

It is certified that error appears in the above-identified patent and that said Letters Patent is hereby corrected as shown below:

Column 38, claim 2,
Line 39, "ina concentration" should read -- in a concentration --.

Column 38, claim 3,
Line 47, in formula (V), "$(R^7)_y(Z)_z$" should read -- $(R^7)_y\text{-}(Z)_z$ --.

Column 39, claim 3,
Line 33, before "x, y and z", delete "z,".

Signed and Sealed this

Ninth Day of April, 2002

Attest:

Attesting Officer

JAMES E. ROGAN
Director of the United States Patent and Trademark Office